(12) United States Patent
Ummalaneni et al.

(10) Patent No.: US 10,827,913 B2
(45) Date of Patent: Nov. 10, 2020

(54) SYSTEMS AND METHODS FOR DISPLAYING ESTIMATED LOCATION OF INSTRUMENT

(71) Applicant: Auris Health, Inc., Redwood City, CA (US)

(72) Inventors: Ritwik Ummalaneni, San Mateo, CA (US); Prasanth Jeevan, San Mateo, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/365,507

(22) Filed: Mar. 26, 2019

(65) Prior Publication Data
US 2019/0298160 A1  Oct. 3, 2019

Related U.S. Application Data

(60) Provisional application No. 62/649,501, filed on Mar. 28, 2018.

(51) Int. Cl.
*A61B 1/00* (2006.01)
*A61B 1/05* (2006.01)
(Continued)

(52) U.S. Cl.
CPC ............... *A61B 1/05* (2013.01); *A61B 5/066* (2013.01); *A61B 34/20* (2016.02); *A61B 2034/2051* (2016.02)

(58) Field of Classification Search
CPC .................................. A61B 1/05; A61B 34/20
See application file for complete search history.

(56) References Cited

U.S. PATENT DOCUMENTS

| 4,745,908 A | 5/1988 | Wardle |
| 5,273,025 A | 12/1993 | Sakiyam et al. |

(Continued)

FOREIGN PATENT DOCUMENTS

| CN | 101147676 | 3/2008 |
| CN | 101222882 | 7/2008 |

(Continued)

OTHER PUBLICATIONS

Ciuti et al,, 2012, Intra-operative monocular 30 reconstruction for image-guided navigation in active locomotion capsule endoscopy. Biomedical Robotics and Biomechatronics (Biorob), 4th IEEE Ras & Embs International Conference on IEEE.

(Continued)

*Primary Examiner* — Joseph M Santos Rodriguez
(74) *Attorney, Agent, or Firm* — Knobbe, Martens, Olson & Bear, LLP

(57) ABSTRACT

Provided are systems and methods for displaying an estimated location of an instrument. In one aspect, the method includes determining a first location of the instrument based on first location data generated by a set of one or more location sensors for the instrument, the first location data corresponding to a first time period, and after the first time period, receiving a user command to move the instrument during a second time period. The method also includes estimating a second location of the instrument based on the first location and the received user command, the estimated second location corresponding to the second time period, and confirming the estimated second location based on second location data generated by the set of location sensors. The method further includes causing the estimated second location to be displayed prior to the confirmation of the estimated second location.

30 Claims, 23 Drawing Sheets

(51) Int. Cl.
   *A61B 34/20* (2016.01)
   *A61B 5/06* (2006.01)

(56) References Cited

U.S. PATENT DOCUMENTS

| | | |
|---|---|---|
| 5,526,812 A | 6/1996 | Dumoulin et al. |
| 5,550,953 A | 8/1996 | Seraji |
| 5,831,614 A | 11/1998 | Tognazzini et al. |
| 5,935,075 A | 8/1999 | Casscells |
| 6,038,467 A | 3/2000 | De Bliek et al. |
| 6,047,080 A | 4/2000 | Chen |
| 6,059,718 A | 5/2000 | Taniguchi et al. |
| 6,063,095 A | 5/2000 | Wang et al. |
| 6,167,292 A | 12/2000 | Badano |
| 6,203,493 B1 | 3/2001 | Ben-Haim |
| 6,246,784 B1 | 6/2001 | Summers |
| 6,246,898 B1 | 6/2001 | Vesely |
| 6,332,089 B1 | 12/2001 | Acker |
| 6,425,865 B1 | 7/2002 | Salcudean et al. |
| 6,466,198 B1 | 10/2002 | Feinstein |
| 6,490,467 B1 | 12/2002 | Bucholz |
| 6,553,251 B1 | 4/2003 | Lahdesmaki |
| 6,665,554 B1 | 12/2003 | Charles |
| 6,690,963 B2 | 2/2004 | Ben-Haim |
| 6,690,964 B2 | 2/2004 | Beiger et al. |
| 6,812,842 B2 | 11/2004 | Dimmer |
| 6,899,672 B2 | 5/2005 | Chin |
| 6,926,709 B2 | 8/2005 | Beiger et al. |
| 7,180,976 B2 | 2/2007 | Wink |
| 7,206,627 B2 | 4/2007 | Abovitz |
| 7,233,820 B2 | 6/2007 | Gilboa |
| 7,386,339 B2 | 6/2008 | Strommer et al. |
| 7,756,563 B2 | 7/2010 | Higgins |
| 7,850,642 B2 | 12/2010 | Moll et al. |
| 7,901,348 B2 | 3/2011 | Soper |
| 8,155,403 B2 | 4/2012 | Tschirren |
| 8,190,238 B2 | 5/2012 | Moll et al. |
| 8,298,135 B2 | 10/2012 | Ito et al. |
| 8,317,746 B2 | 11/2012 | Sewell et al. |
| 8,394,054 B2 | 3/2013 | Wallace et al. |
| 8,460,236 B2 | 6/2013 | Roelle et al. |
| 8,821,376 B2 | 9/2014 | Tolkowsky |
| 8,858,424 B2 | 10/2014 | Hasegawa |
| 8,929,631 B2 | 1/2015 | Pfister et al. |
| 9,014,851 B2 | 4/2015 | Wong et al. |
| 9,125,639 B2 | 9/2015 | Mathis |
| 9,138,129 B2 | 9/2015 | Diolaiti |
| 9,183,354 B2 | 11/2015 | Baker et al. |
| 9,186,046 B2 | 11/2015 | Ramamurthy et al. |
| 9,272,416 B2 | 3/2016 | Hourtash et al. |
| 9,289,578 B2 | 3/2016 | Walker et al. |
| 9,459,087 B2 | 10/2016 | Dunbar |
| 9,504,604 B2 | 11/2016 | Alvarez |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,717,563 B2 | 8/2017 | Tognaccini |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,278,778 B2 | 5/2019 | State |
| 10,524,866 B2 | 1/2020 | Srinivasan |
| 10,639,114 B2 | 5/2020 | Schuh |
| 10,667,875 B2 | 6/2020 | DeFonzo |
| 2001/0021843 A1 | 9/2001 | Bosselmann et al. |
| 2001/0039421 A1 | 11/2001 | Heilbrun |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0186349 A1 | 9/2004 | Ewers |
| 2004/0249267 A1 | 12/2004 | Gilboa |
| 2004/0263535 A1 | 12/2004 | Birkenbach et al. |
| 2005/0027397 A1 | 2/2005 | Niemeyer |
| 2005/0060006 A1 | 3/2005 | Pflueger |
| 2005/0085714 A1 | 4/2005 | Foley et al. |
| 2005/0107679 A1 | 5/2005 | Geiger |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0193451 A1 | 9/2005 | Quistgaard et al. |
| 2005/0256398 A1 | 11/2005 | Hastings |
| 2005/0272975 A1 | 12/2005 | McWeeney et al. |
| 2006/0004286 A1 | 1/2006 | Chang |
| 2006/0015096 A1 | 1/2006 | Hauck et al. |
| 2006/0025668 A1 | 2/2006 | Peterson |
| 2006/0058643 A1 | 3/2006 | Florent |
| 2006/0084860 A1 | 4/2006 | Geiger |
| 2006/0095066 A1 | 5/2006 | Chang |
| 2006/0098851 A1 | 5/2006 | Shoham |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0032826 A1 | 2/2007 | Schwartz |
| 2007/0055128 A1 | 3/2007 | Glossop |
| 2007/0055144 A1 | 3/2007 | Neustadter |
| 2007/0073136 A1 | 3/2007 | Metzger |
| 2007/0083193 A1 | 4/2007 | Werneth |
| 2007/0123748 A1 | 5/2007 | Meglan |
| 2007/0135886 A1 | 6/2007 | Maschke |
| 2007/0156019 A1 | 7/2007 | Larkin et al. |
| 2007/0167801 A1 | 7/2007 | Webler et al. |
| 2007/0208252 A1 | 9/2007 | Makower |
| 2007/0253599 A1 | 11/2007 | White et al. |
| 2007/0269001 A1 | 11/2007 | Maschke |
| 2007/0293721 A1 | 12/2007 | Gilboa |
| 2007/0299353 A1 | 12/2007 | Harley et al. |
| 2008/0071140 A1 | 3/2008 | Gattani |
| 2008/0079421 A1 | 4/2008 | Jensen |
| 2008/0103389 A1 | 5/2008 | Begelman et al. |
| 2008/0118118 A1 | 5/2008 | Berger |
| 2008/0118135 A1 | 5/2008 | Averbach |
| 2008/0123921 A1 | 5/2008 | Gielen et al. |

(56) References Cited

U.S. PATENT DOCUMENTS

| | | |
|---|---|---|
| 2008/0161681 A1 | 7/2008 | Hauck |
| 2008/0183064 A1 | 7/2008 | Chandonnet |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0243142 A1 | 10/2008 | Gildenberg |
| 2008/0262297 A1 | 10/2008 | Gilboa |
| 2008/0275349 A1 | 11/2008 | Halperin |
| 2008/0287963 A1 | 11/2008 | Rogers et al. |
| 2008/0306490 A1 | 12/2008 | Lakin et al. |
| 2008/0312501 A1 | 12/2008 | Hasegawa et al. |
| 2009/0030307 A1 | 1/2009 | Govari |
| 2009/0054729 A1 | 2/2009 | Mori |
| 2009/0076476 A1 | 3/2009 | Barbagli et al. |
| 2009/0227861 A1 | 9/2009 | Ganatra |
| 2009/0248036 A1 | 10/2009 | Hoffman et al. |
| 2009/0259230 A1 | 10/2009 | Khadem |
| 2009/0262109 A1 | 10/2009 | Markowitz et al. |
| 2009/0295797 A1 | 12/2009 | Sakaguchi |
| 2010/0008555 A1 | 1/2010 | Trumer |
| 2010/0039506 A1 | 2/2010 | Sarvestani et al. |
| 2010/0041949 A1 | 2/2010 | Tolkowsky |
| 2010/0054536 A1 | 3/2010 | Huang |
| 2010/0113852 A1 | 5/2010 | Sydora |
| 2010/0121139 A1 | 5/2010 | OuYang |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0298641 A1 | 11/2010 | Tanaka |
| 2010/0328455 A1 | 12/2010 | Nam et al. |
| 2011/0054303 A1 | 3/2011 | Barrick |
| 2011/0092808 A1 | 4/2011 | Shachar |
| 2011/0184238 A1 | 7/2011 | Higgins |
| 2011/0234780 A1 | 9/2011 | Ito |
| 2011/0238082 A1 | 9/2011 | Wenderow |
| 2011/0245665 A1 | 10/2011 | Nentwick |
| 2011/0248987 A1 | 10/2011 | Mitchell |
| 2011/0249016 A1 | 10/2011 | Zhang et al. |
| 2011/0276179 A1 | 11/2011 | Banks et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0065481 A1 | 3/2012 | Hunter |
| 2012/0069167 A1 | 3/2012 | Liu et al. |
| 2012/0071782 A1 | 3/2012 | Patil et al. |
| 2012/0082351 A1 | 4/2012 | Higgins |
| 2012/0120305 A1 | 5/2012 | Takahashi |
| 2012/0165656 A1 | 6/2012 | Montag |
| 2012/0191079 A1 | 7/2012 | Moll et al. |
| 2012/0209069 A1 | 8/2012 | Popovic |
| 2012/0215094 A1 | 8/2012 | Rahimian et al. |
| 2012/0219185 A1 | 8/2012 | Hu |
| 2012/0289783 A1 | 11/2012 | Duindam et al. |
| 2012/0302869 A1 | 11/2012 | Koyrakh |
| 2013/0060146 A1 | 3/2013 | Yang et al. |
| 2013/0144116 A1 | 6/2013 | Cooper et al. |
| 2013/0165945 A9 | 6/2013 | Roelle |
| 2013/0243153 A1 | 9/2013 | Sra |
| 2013/0246334 A1 | 9/2013 | Ahuja |
| 2013/0259315 A1 | 10/2013 | Angot et al. |
| 2013/0345718 A1 | 12/2013 | Crawford |
| 2014/0058406 A1 | 2/2014 | Tsekos |
| 2014/0114180 A1 | 4/2014 | Jain |
| 2014/0142591 A1 | 5/2014 | Alvarez et al. |
| 2014/0148808 A1 | 5/2014 | Inkpen et al. |
| 2014/0180063 A1 | 6/2014 | Zhao |
| 2014/0243849 A1 | 8/2014 | Saglam |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276937 A1 | 9/2014 | Wong et al. |
| 2014/0296655 A1 | 10/2014 | Akhbardeh et al. |
| 2014/0309527 A1 | 10/2014 | Namati et al. |
| 2014/0350391 A1 | 11/2014 | Prisco et al. |
| 2014/0357984 A1 | 12/2014 | Wallace et al. |
| 2014/0364739 A1 | 12/2014 | Liu |
| 2014/0364870 A1 | 12/2014 | Alvarez et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto |
| 2015/0073266 A1 | 3/2015 | Brannan |
| 2015/0141808 A1 | 5/2015 | Elhawary |
| 2015/0141858 A1 | 5/2015 | Razavi |
| 2015/0142013 A1 | 5/2015 | Tanner et al. |
| 2015/0164594 A1 | 6/2015 | Romo et al. |
| 2015/0164596 A1 | 6/2015 | Romo |
| 2015/0223725 A1 | 8/2015 | Engel |
| 2015/0223897 A1 | 8/2015 | Kostrzewski et al. |
| 2015/0223902 A1 | 8/2015 | Walker et al. |
| 2015/0265368 A1 | 9/2015 | Chopra |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0313503 A1* | 11/2015 | Seibel ............... A61B 1/00165 600/103 |
| 2015/0335480 A1 | 11/2015 | Alvarez et al. |
| 2016/0000520 A1 | 1/2016 | Lachmanovich |
| 2016/0001038 A1 | 1/2016 | Romo et al. |
| 2016/0008033 A1 | 1/2016 | Hawkins et al. |
| 2016/0111192 A1 | 4/2016 | Suzara |
| 2016/0128992 A1 | 5/2016 | Hudson |
| 2016/0199134 A1 | 7/2016 | Brown et al. |
| 2016/0206389 A1 | 7/2016 | Miller |
| 2016/0213432 A1 | 7/2016 | Flexman |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0314710 A1 | 10/2016 | Jarc |
| 2016/0331469 A1 | 11/2016 | Hall et al. |
| 2016/0360947 A1 | 12/2016 | Iida |
| 2016/0374541 A1 | 12/2016 | Aarawal et al. |
| 2017/0007337 A1 | 1/2017 | Dan |
| 2017/0055851 A1 | 3/2017 | Al-Ali |
| 2017/0079725 A1 | 3/2017 | Hoffman |
| 2017/0079726 A1 | 3/2017 | Hoffman |
| 2017/0100199 A1 | 4/2017 | Yu et al. |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0238807 A9 | 8/2017 | Vertikov et al. |
| 2017/0258366 A1 | 9/2017 | Tupin |
| 2017/0290631 A1 | 10/2017 | Lee et al. |
| 2017/0296032 A1 | 10/2017 | Li |
| 2017/0296202 A1 | 10/2017 | Brown |
| 2017/0325896 A1 | 11/2017 | Donhowe |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360508 A1 | 12/2017 | Germain et al. |
| 2017/0367782 A1 | 12/2017 | Schuh et al. |
| 2018/0025666 A1 | 1/2018 | Ho et al. |
| 2018/0055582 A1 | 3/2018 | Krimsky |
| 2018/0098690 A1 | 4/2018 | Iwaki |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0217734 A1 | 8/2018 | Koenig et al. |

(56) References Cited

U.S. PATENT DOCUMENTS

| | | |
|---|---|---|
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289243 A1 | 10/2018 | Landey et al. |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0046814 A1 | 2/2019 | Senden et al. |
| 2019/0066314 A1 | 2/2019 | Abhari |
| 2019/0083183 A1 | 3/2019 | Moll et al. |
| 2019/0086349 A1 | 3/2019 | Nelson |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0117176 A1 | 4/2019 | Walker et al. |
| 2019/0117203 A1 | 4/2019 | Wong et al. |
| 2019/0151148 A1 | 4/2019 | Alvarez et al. |
| 2019/0125164 A1 | 5/2019 | Roelle et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata |
| 2019/0290109 A1 | 9/2019 | Agrawal et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0155084 A1 | 5/2020 | Walker |

FOREIGN PATENT DOCUMENTS

| | | |
|---|---|---|
| CN | 102316817 | 1/2012 |
| CN | 102458295 | 5/2012 |
| CN | 102973317 | 3/2013 |
| CN | 103735313 | 4/2014 |
| CN | 105559850 | 5/2016 |
| CN | 105559886 | 5/2016 |
| CN | 105611881 | 5/2016 |
| CN | 106821498 | 6/2017 |
| CN | 104931059 | 9/2018 |
| EP | 3 025 630 | 6/2016 |
| KR | 10-2014-0009359 | 1/2014 |
| RU | 2569699 C2 | 11/2015 |
| WO | WO 09/097461 | 6/2007 |
| WO | WO 15/089013 | 6/2015 |
| WO | WO 17/048194 | 3/2017 |
| WO | WO 17/066108 | 4/2017 |
| WO | WO 17/167754 | 10/2017 |

OTHER PUBLICATIONS

Fallavollita et al., 2010, Acquiring multiview C-arm images to assist cardiac ablation procedures, EURASIP Journal on Image and Video Processing, vol. 2010, Article ID 871408, pp. 1-10.

Haigron et al., 2004, Depth-map-based scene analysis for active navigation in virtual angioscopy, IEEE Transactions on Medical Imaging, 23(11):1380-1390.

Kumar et al., 2014, Stereoscopic visualization of laparoscope image using depth information from 3D model, Computer methods and programs in biomedicine 113(3):862-868.

Livatino et al., 2015, Stereoscopic visualization and 3-D technologies in medical endoscopic teleoperation, IEEE.

Luo et al., 2010, Modified hybrid bronchoscope tracking based on sequential monte carlo sampler: Dynamic phantom validation, Asian Conference on Computer Vision. Springer, Berlin, Heidelberg.

Mayo Clinic, Robotic Surgery, https://www.mayoclinic.org/tests-procedures/robotic-surgery/about/pac-20394974?p=1, downloaded from the internet on Jul. 12, 2018, 2 pp.

Mourgues et al., 2002, Flexible calibration of actuated stereoscopic endoscope for overlay inrobot assisted surgery, International Conference on Medical Image Computing and Computer-Assisted Intervention, Springer, Berlin, Heidelberg.

Nadeem et al., 2016, Depth Reconstruction and Computer-Aided Polyp Detection in Optical Colonoscopy Video Frames, arXiv preprint arXiv:1609.01329.

Point Cloud, Sep. 10, 2010, Wikipedia, 2 pp.

Racadio et al., Dec. 2007, Live 3D guidance in the interventional radiology suite, AJR, 189:W357-W364.

Sato et al., 2016, Techniques of stapler-based navigational thoracoscopic segmentectomy using virtual assisted lung mapping (VAL-MAP), Journal of Thoracic Disease, 8(Suppl 9):S716.

Shen et al., 2015, Robust camera localisation with depth reconstruction for bronchoscopic navigation. International Journal of Computer Assisted Radiology and Surgery, 10(6):801-813.

Solheim et al., May 14, 2009, Navigated resection of giant intracranial meningiomas based on intraoperative 3D ultrasound, Acta Neurochir, 151:1143-1151.

Song et al., 2012, Autonomous and stable tracking of endoscope instrument tools with monocular camera, Advanced Intelligent Mechatronics (AIM), 2012 IEEE-ASME International Conference on. IEEE.

Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.

Yip et al., 2012, Tissue tracking and registration for image-guided surgery, IEEE transactions on medical imaging 31(11):2169-2182.

(56) References Cited

OTHER PUBLICATIONS

Zhou et al., 2010, Synthesis of stereoscopic views from monocular endoscopic videos, Computer Vision and Pattern Recognition Workshops (CVPRW), 2010 IEEE Computer Society Conference on IEEE.

Konen et al., 1998, The VN-project: endoscopic image processing for neurosurgery, COmputer Aided Surgery, 3:1-6.

Shi et al., Sep. 14-18, 2014, Simultaneous catheter and environment modeling for trans-catheter aortic valve implantation, IEEE/RSJ International Conference on Intelligent Robots and Systems, pp. 2024-2029.

Vemuri et al., Dec. 2015, Inter-operative biopsy site relocations in endoluminal surgery, IEEE Transactions on Biomedical Engineering, Institute of Electrical and Electronics Engineers, <10.1109/TBME.2015.2503981>. <hal-01230752>.

Wilson et al., 2008, a buyer's guide to electromagnetic tracking systems for clinical applications, Proc. of SPCI, 6918:69182B-1 p. 6918B-11.

International search report and written opinion dated Jun. 11, 2019 for PCT/US2019/24146.

Al-Ahmad et al., dated 2005, Early experience with a computerized robotically controlled catheter system, Journal of Interventional Cardiac Electrophysiology, 12:199-202.

Hansen Medical, Inc. Bibliography, product brochure, 1 p., dated as available at http://hansenmedical.com/bibliography.aspx on Jul. 14, 2006 (accessed Jun. 25, 2019 using the internet archive way back machine).

Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).

Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).

Hansen Medical, Inc. dated 2007, Introducing the Sensei Robotic Catheter System, product brochure, 10 pp.

Hansen Medical, Inc. dated 2009, Sensei X Robotic Catheter System, product brochure, 5 pp.

Kiraly et al, 2002, Three-dimensional Human Airway Segmentation Methods for Clinical Virtual Bronchoscopy, Acad Radiol, 9:1153-1168.

Kiraly et al., Sep. 2004, Three-dimensional path planning for virtual bronchoscopy, IEEE Transactions on Medical Imaging, 23(9):1365-1379.

Marrouche et al., dated May 6, 2005, AB32-1, Preliminary human experience using a novel robotic catheter remote control, Heart Rhythm, 2(5):S63.

Oh et al., dated May 2005, p. 5-75, Novel robotic catheter remote control system: safety and accuracy in delivering RF Lesions in all 4 cardiac chambers, Heart Rhythm, 2(5):S278-S279.

Reddy et al., May 2005, p. 1-53. Porcine pulmonary vein ablation using a novel robotic catheter control system and real-time integration of CT imaging with electroanatomical mapping, Hearth Rhythm, 2(5):S121.

Slepian, dated 2010, Robotic Catheter Intervention: the Hansen Medical Sensei Robot Catheter System, PowerPoint presentation, 28 pp.

Solomon et al., Dec. 2000, Three-dimensional CT—Guided Bronchoscopy With a Real-Time Electromagnetic Position Sensor A Comparison of Two Image Registration Methods, Chest, 118(6):1783-1787.

* cited by examiner

SYSTEMS AND METHODS FOR DISPLAYING ESTIMATED LOCATION OF INSTRUMENT

CROSS-REFERENCE TO RELATED APPLICATION

This application claims the benefit of U.S. Provisional Application No. 62/649,501, filed Mar. 28, 2018, which is hereby incorporated by reference in its entirety.

TECHNICAL FIELD

The systems and methods disclosed herein are directed to displaying an estimated location of an instrument, and more particularly to techniques for compensating for latency in the display of the instrument's location.

BACKGROUND

Medical procedures such as endoscopy (e.g., bronchoscopy) may involve the insertion of a medical tool into a patient's luminal network (e.g., airways) for diagnostic and/or therapeutic purposes. Surgical robotic systems may be used to control the insertion and/or manipulation of the medical tool during a medical procedure. The surgical robotic system may comprise at least one robotic arm including a manipulator assembly which may be used to control the positioning of the medical tool prior to and during the medical procedure. The surgical robotic system may further comprise location sensor(s) configured to generate location data indicative of a position of the distal end of the medical tool.

The surgical robotic system may further comprise one or more displays for providing an indication of the location of the distal end of the instrument to a user. The display may be configured to display the position of the distal end of the instrument in "real-time" as the instrument is navigated through the luminal network to track movement and current location of the instrument. However, there may be a certain amount of latency associated with the display of the instrument's position.

SUMMARY

The systems, methods and devices of this disclosure each have several innovative aspects, no single one of which is solely responsible for the desirable attributes disclosed herein.

In one aspect, there is provided a system, comprising a processor, and at least one computer-readable memory in communication with the processor and having stored thereon computer-executable instructions to cause the processor to: determine a first location of an instrument based on first location data generated by a set of one or more location sensors for the instrument, the first location data corresponding to a first time period; after the first time period, receive a user command to move the instrument during a second time period; estimate a second location of the instrument based on the first location and the received user command, the estimated second location corresponding to the second time period; confirm the estimated second location based on second location data generated by the set of location sensors, the second location data corresponding to the second time period; and cause the estimated second location to be displayed prior to the confirmation of the estimated second location.

In another aspect, there is provided a non-transitory computer readable storage medium having stored thereon instructions that, when executed, cause at least one computing device to: determine a first location of an instrument based on first location data generated by a set of one or more location sensors for the instrument, the first location data corresponding to a first time period; after the first time period, receive a user command to move the instrument during a second time period; estimate a second location of the instrument based on the first location and the received user command, the estimated second location corresponding to the second time period; confirm the estimated second location based on second location data generated by the set of location sensors, the second location data corresponding to the second time period; and cause the estimated second location to be displayed prior to the confirmation of the estimated second location.

In yet another aspect, there is provided a method of displaying an estimated location of an instrument, comprising: determining a first location of the instrument based on first location data generated by a set of one or more location sensors for the instrument, the first location data corresponding to a first time period; after the first time period, receiving a user command to move the instrument during a second time period; estimating a second location of the instrument based on the first location and the received user command, the estimated second location corresponding to the second time period; confirming the estimated second location based on second location data generated by the set of location sensors, the second location data corresponding to the second time period; and causing the estimated second location to be displayed prior to the confirmation of the estimated second location.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
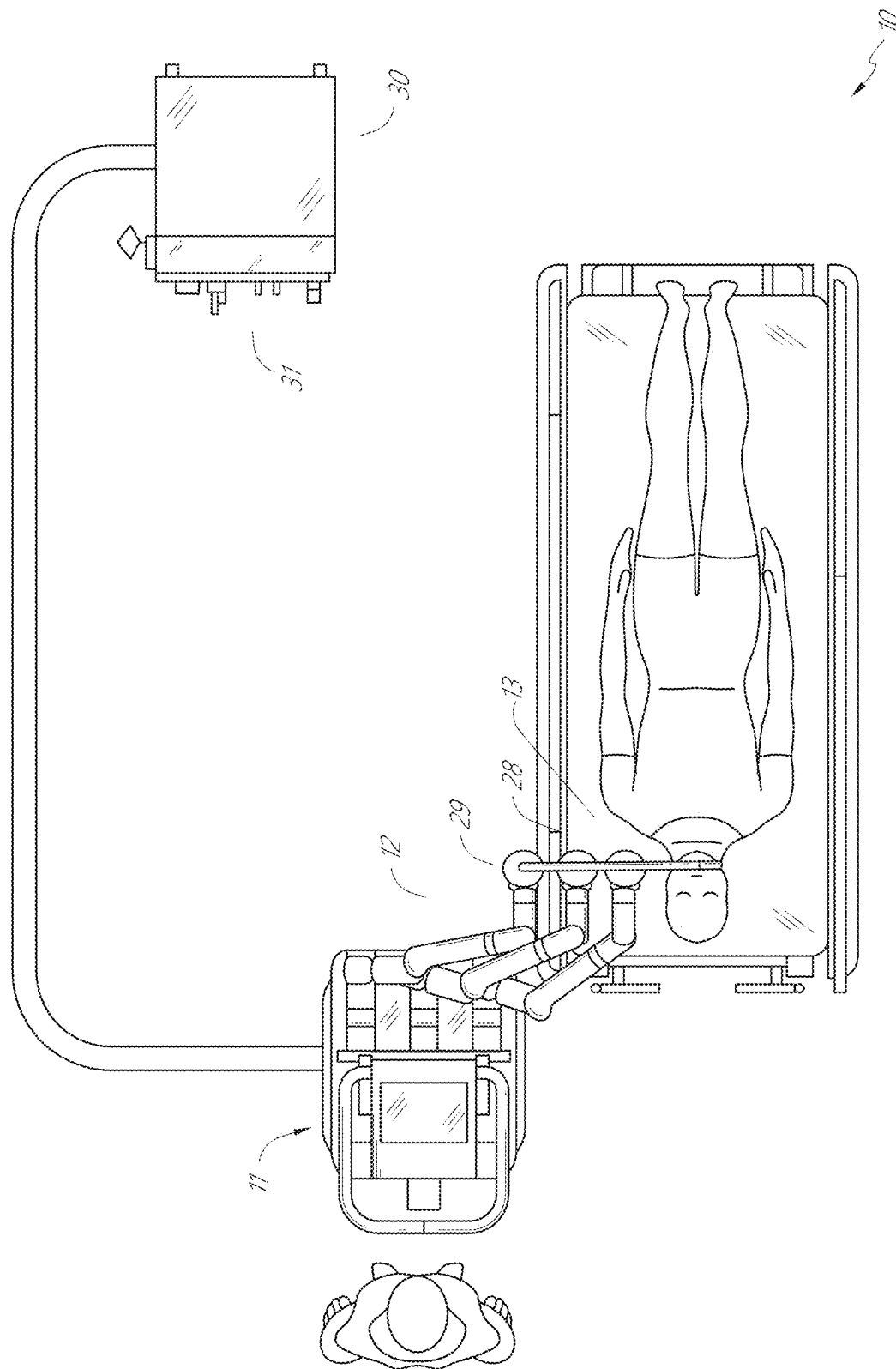
FIG. 1 illustrates an embodiment of a cart-based robotic system arranged for diagnostic and/or therapeutic bronchoscopy procedure(s).
Figure 2:
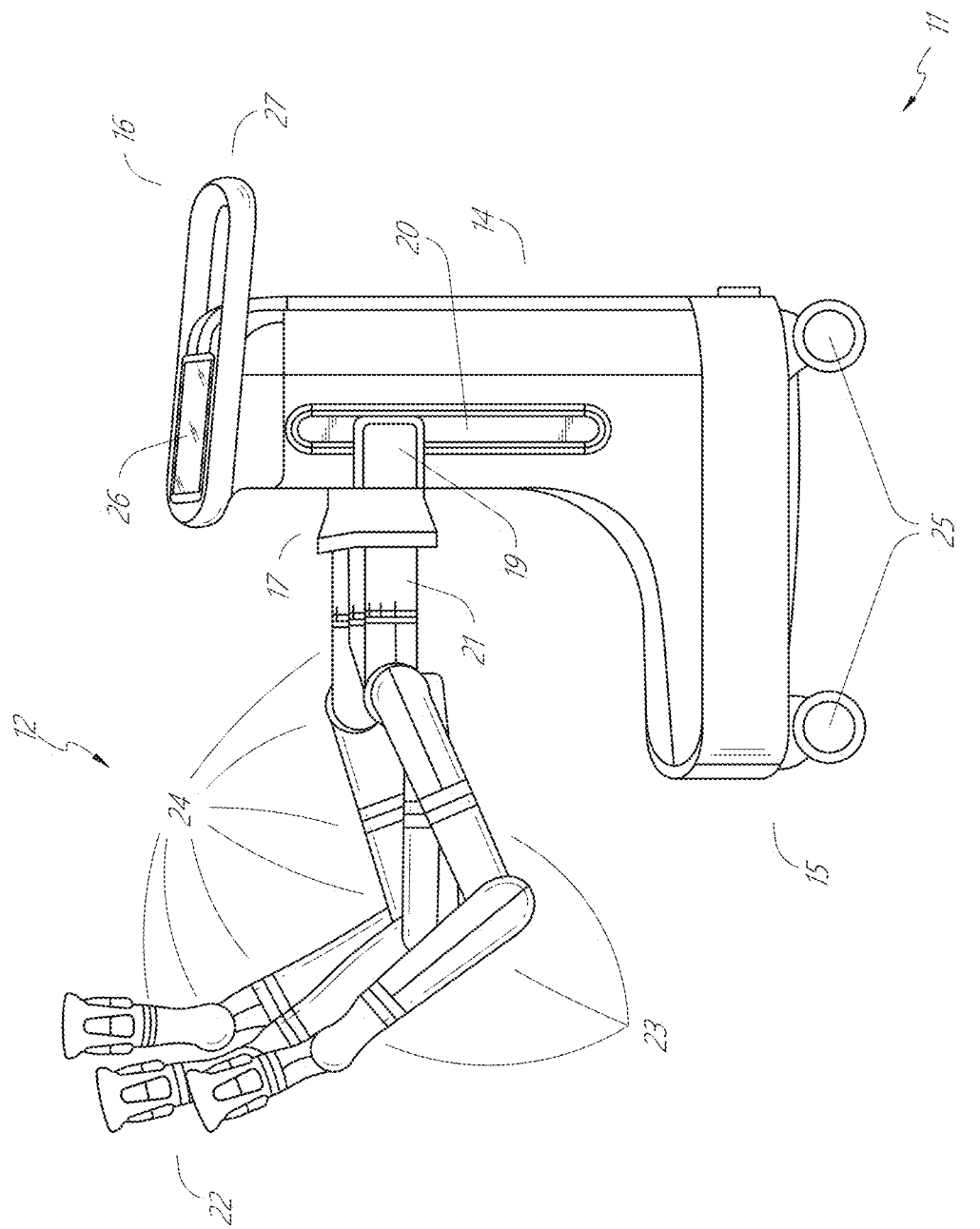
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
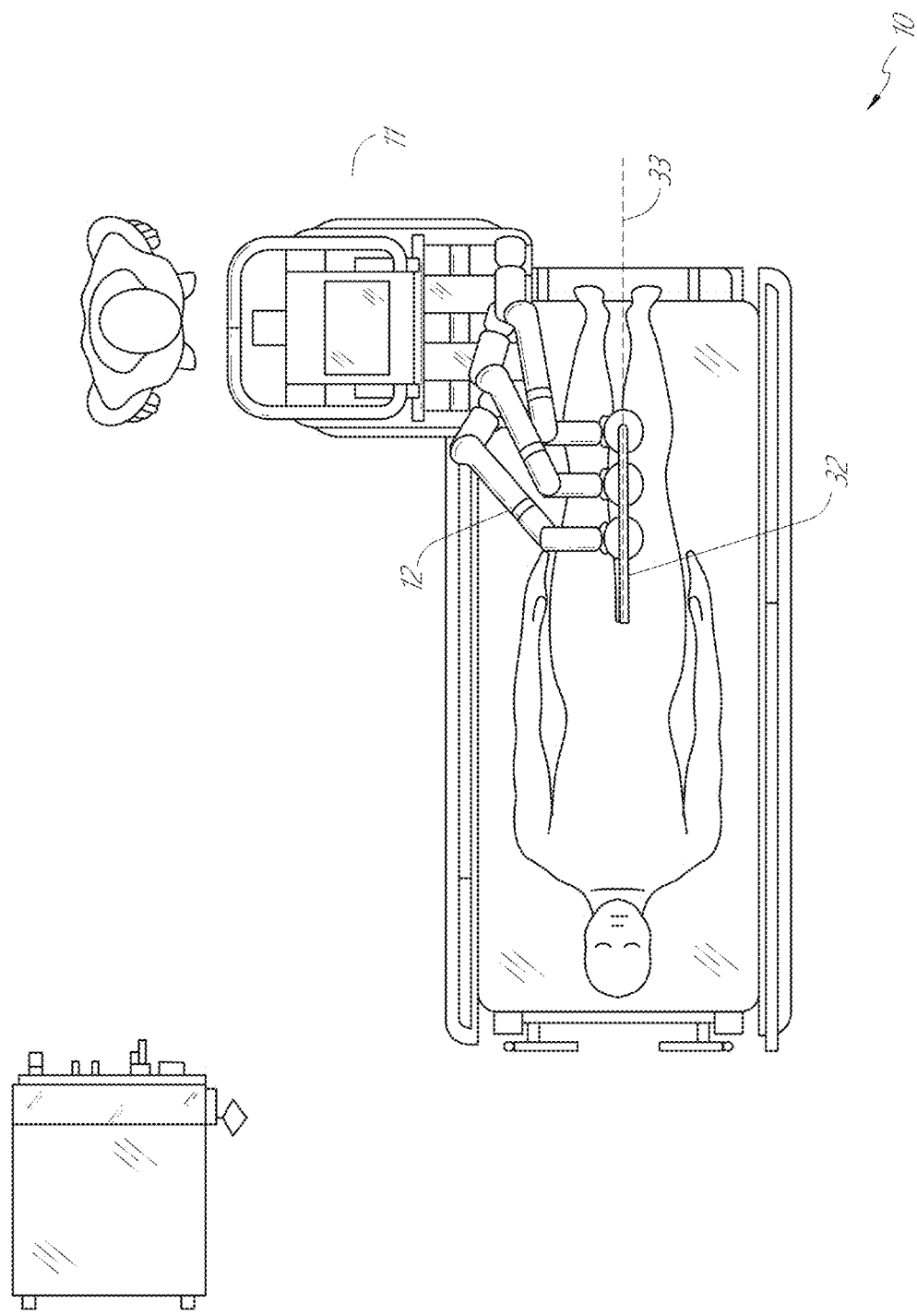
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
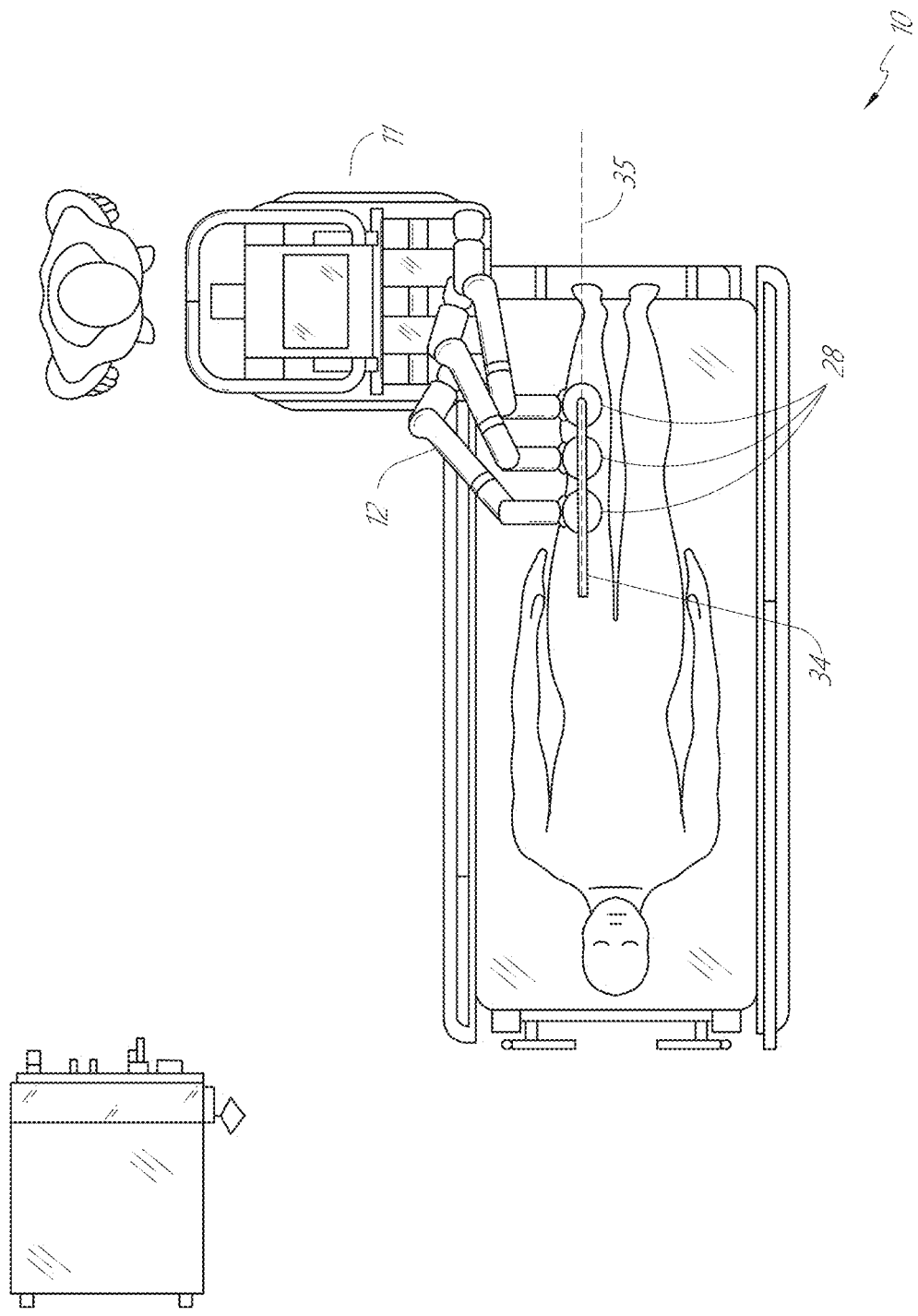
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
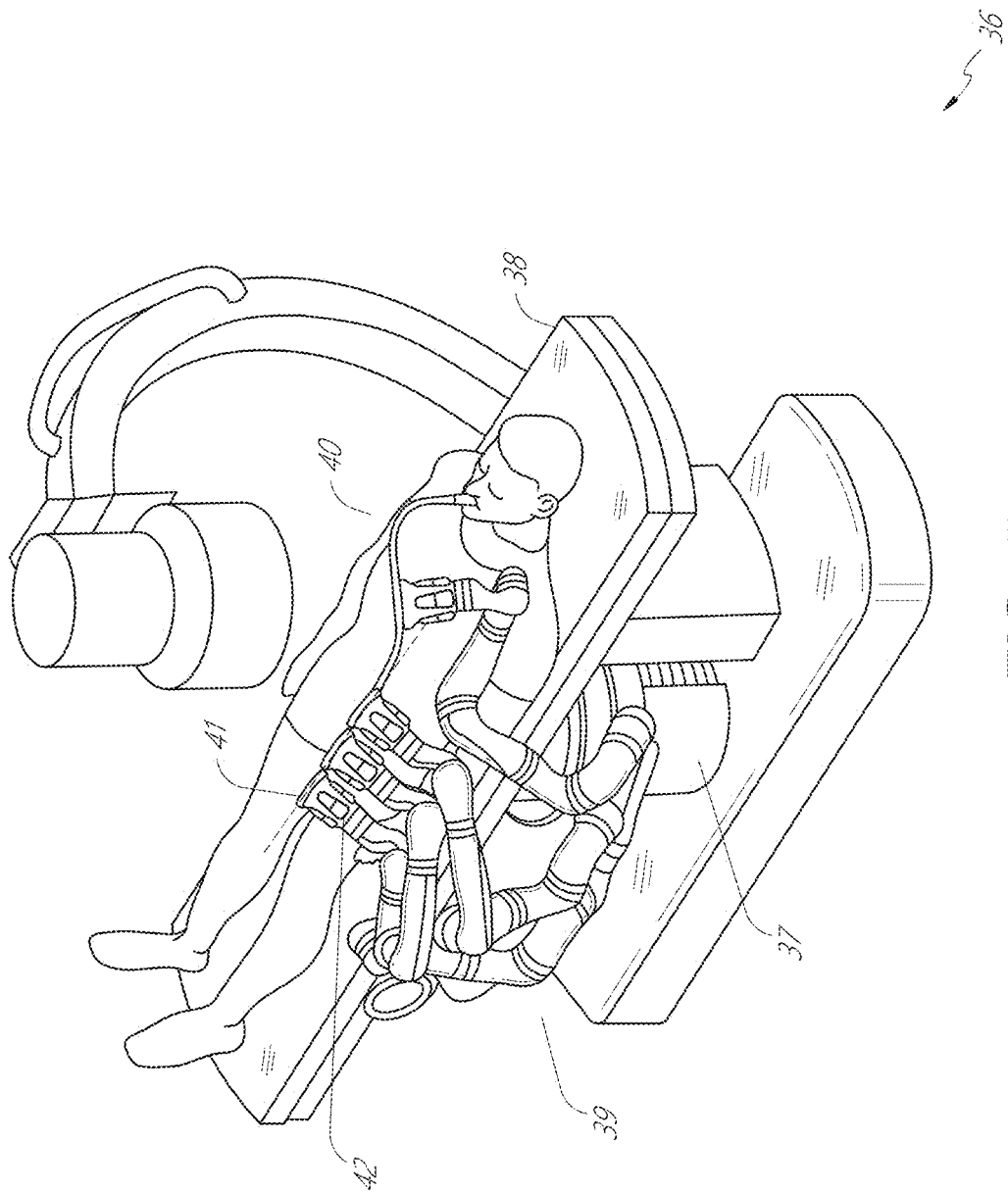
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
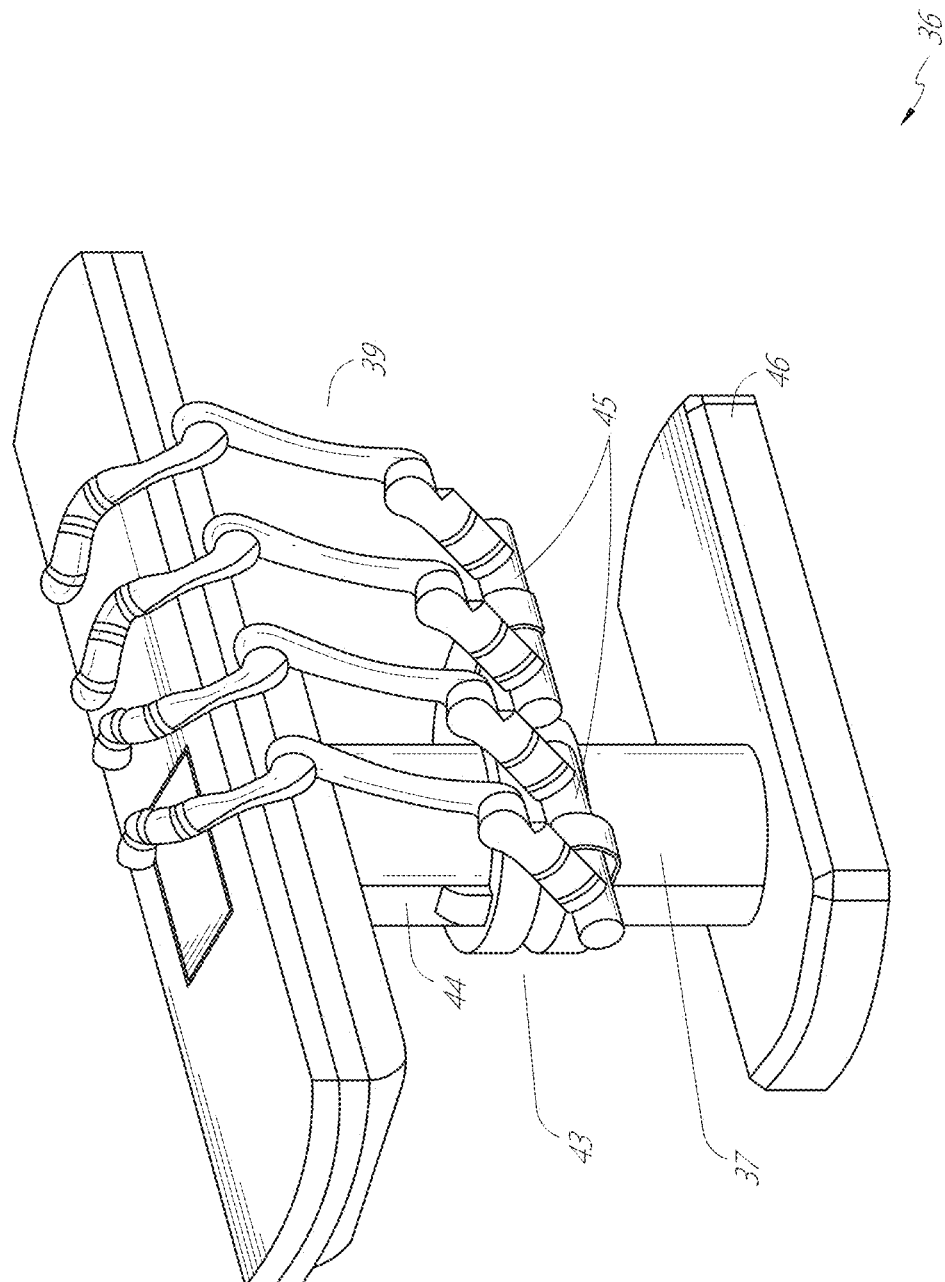
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient.

Figure 9:
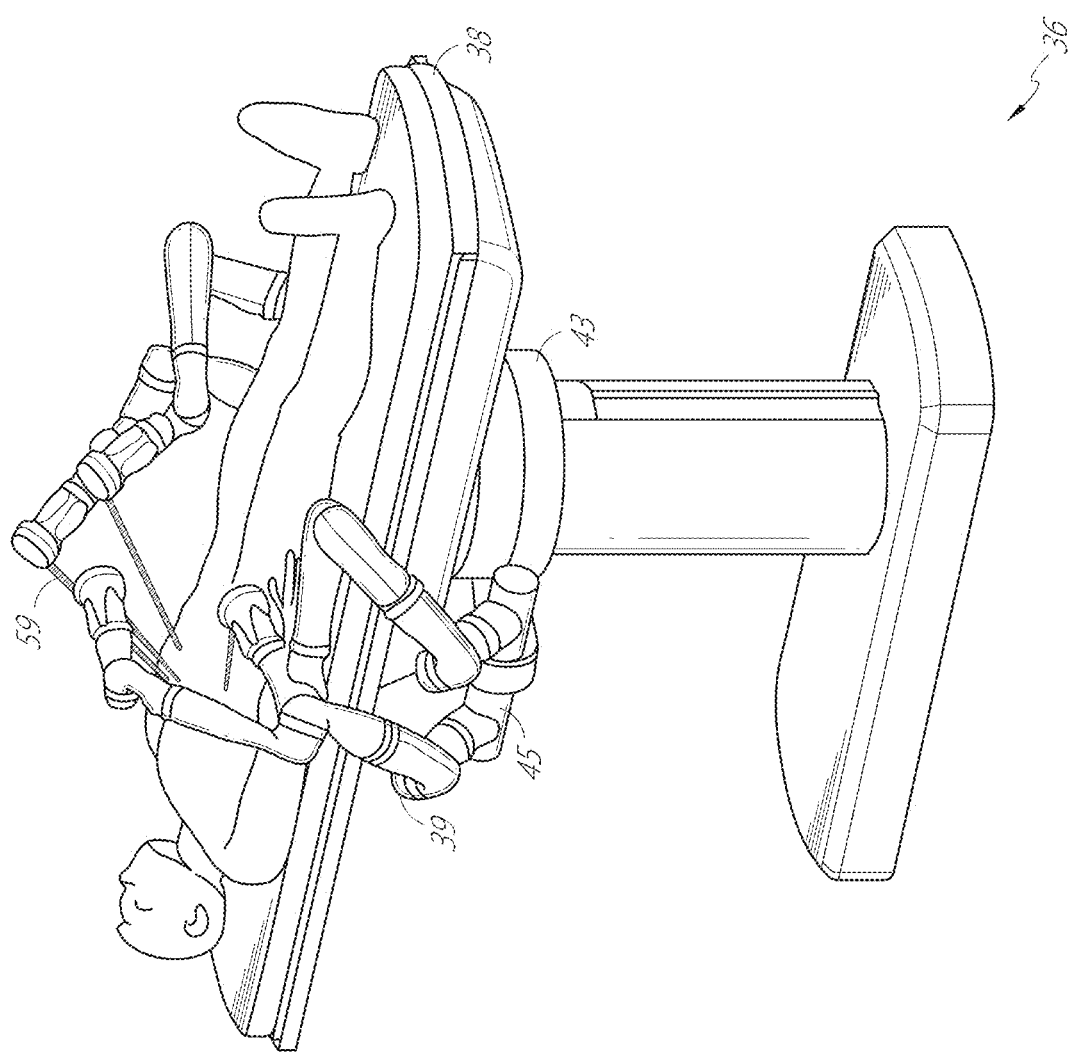
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a console that provides both a user interface for user input, such as keyboard and/or pendant, as well as a display screen (or touchscreen) for pre-operative and intra-operative information, such as real-time imaging, navigation, and tracking information.

Figure 7:
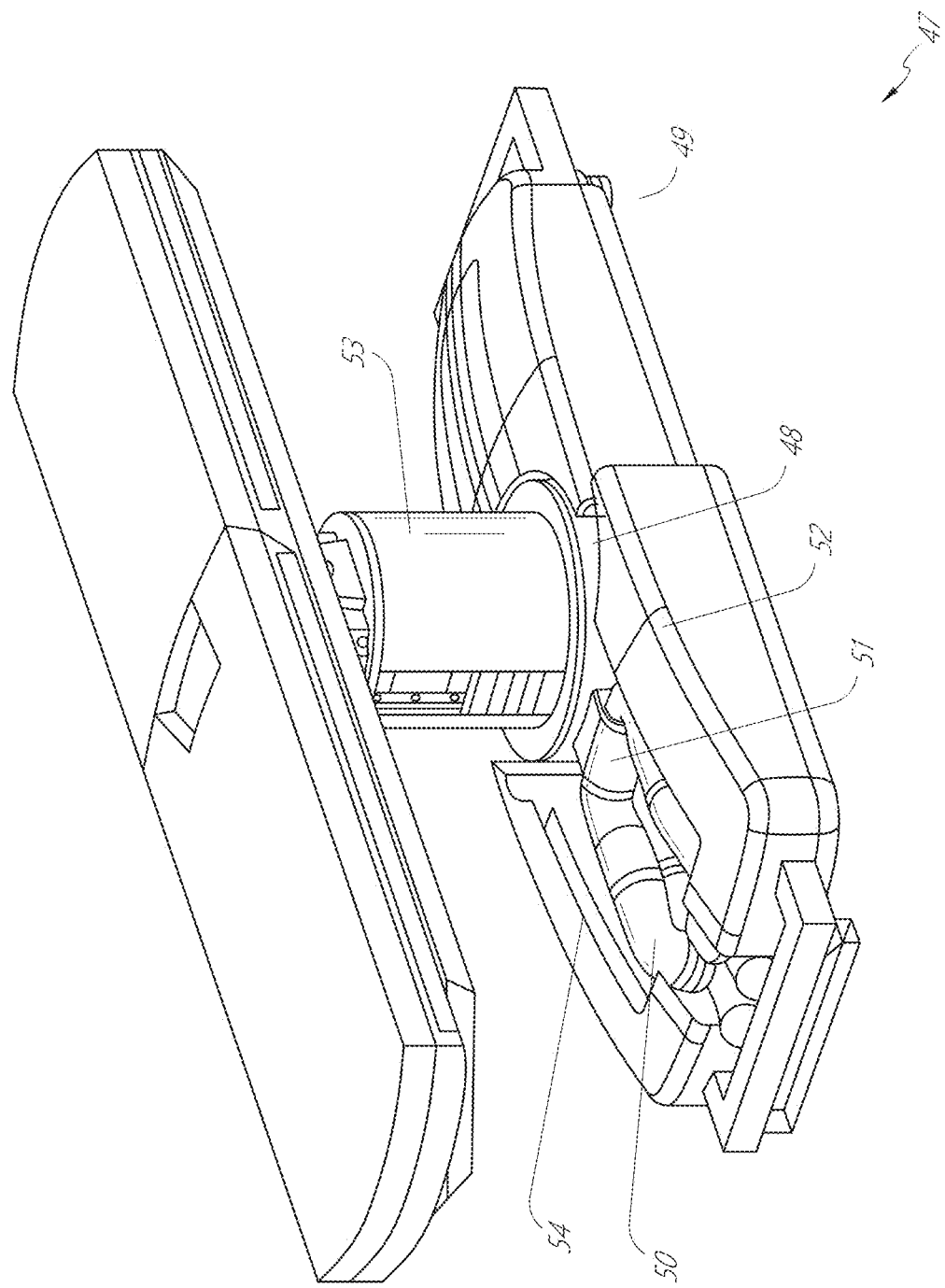
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
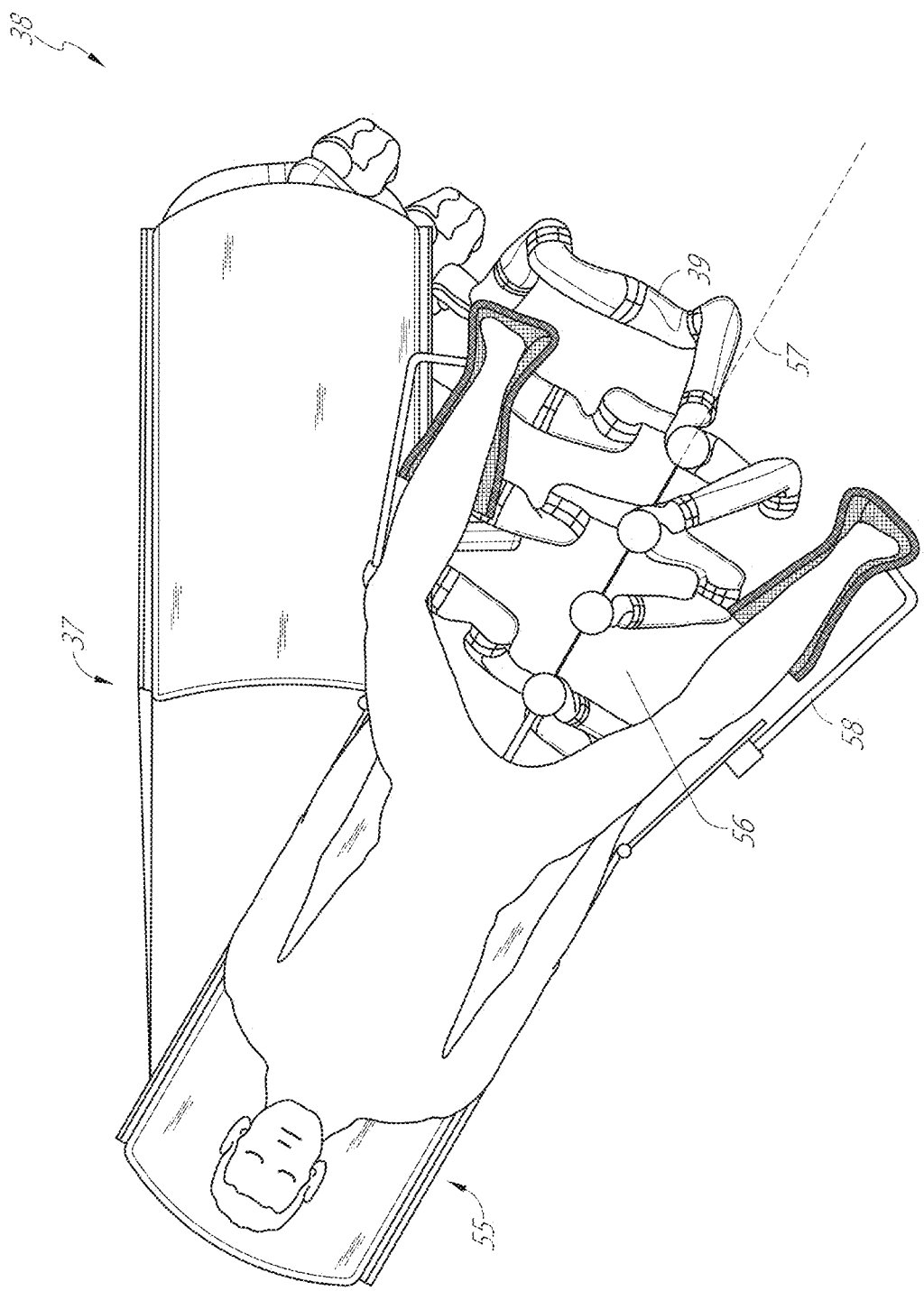
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
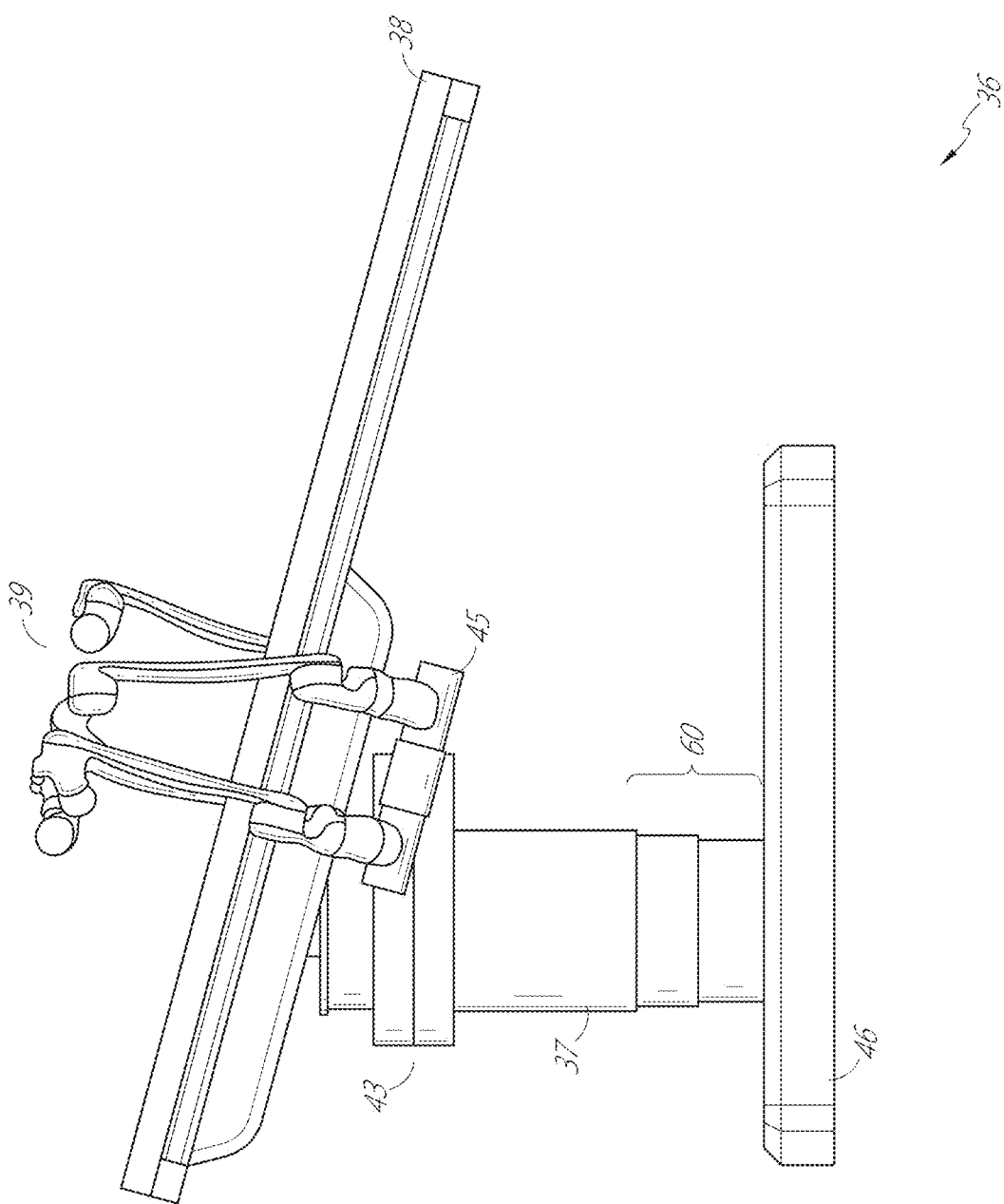
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
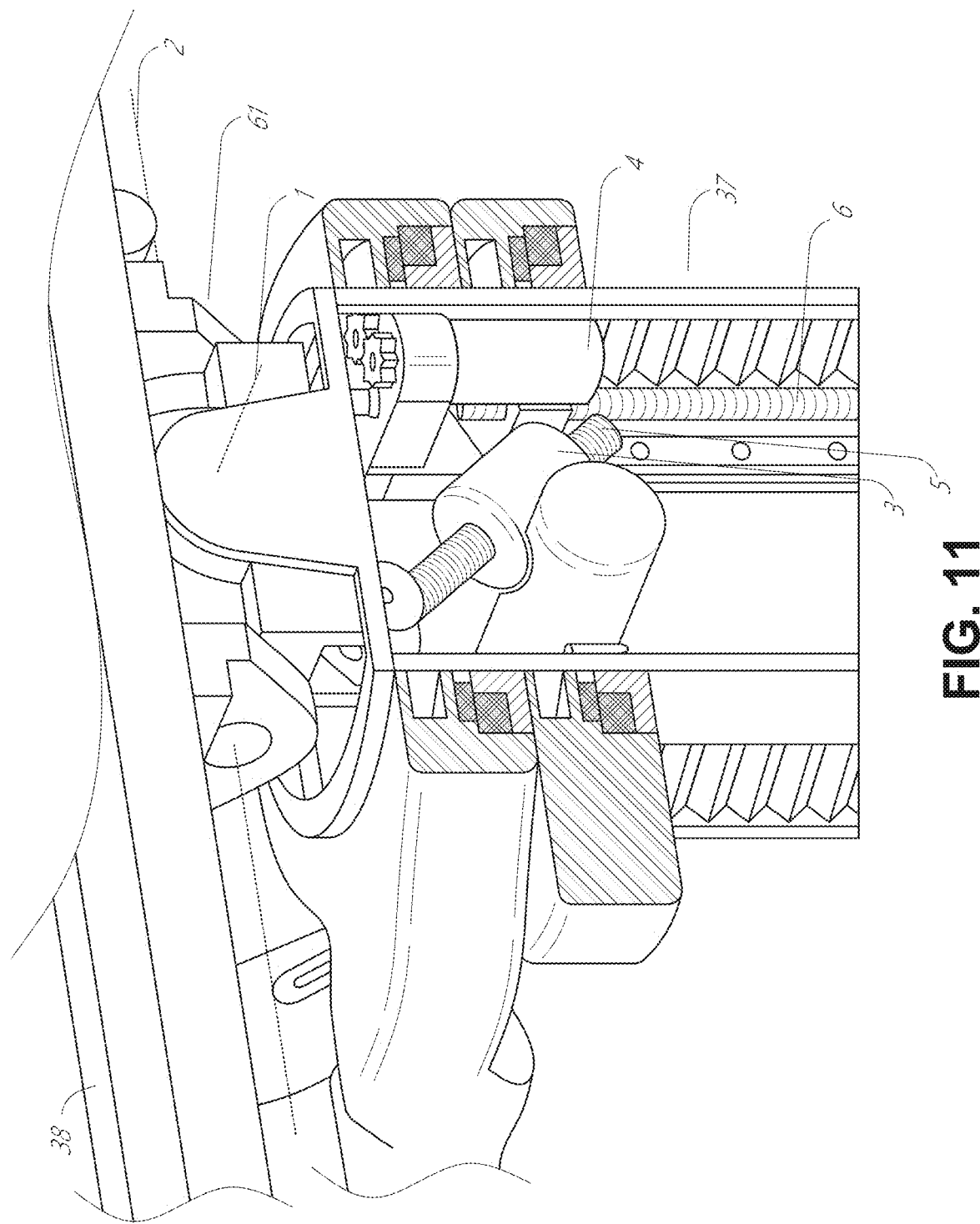
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
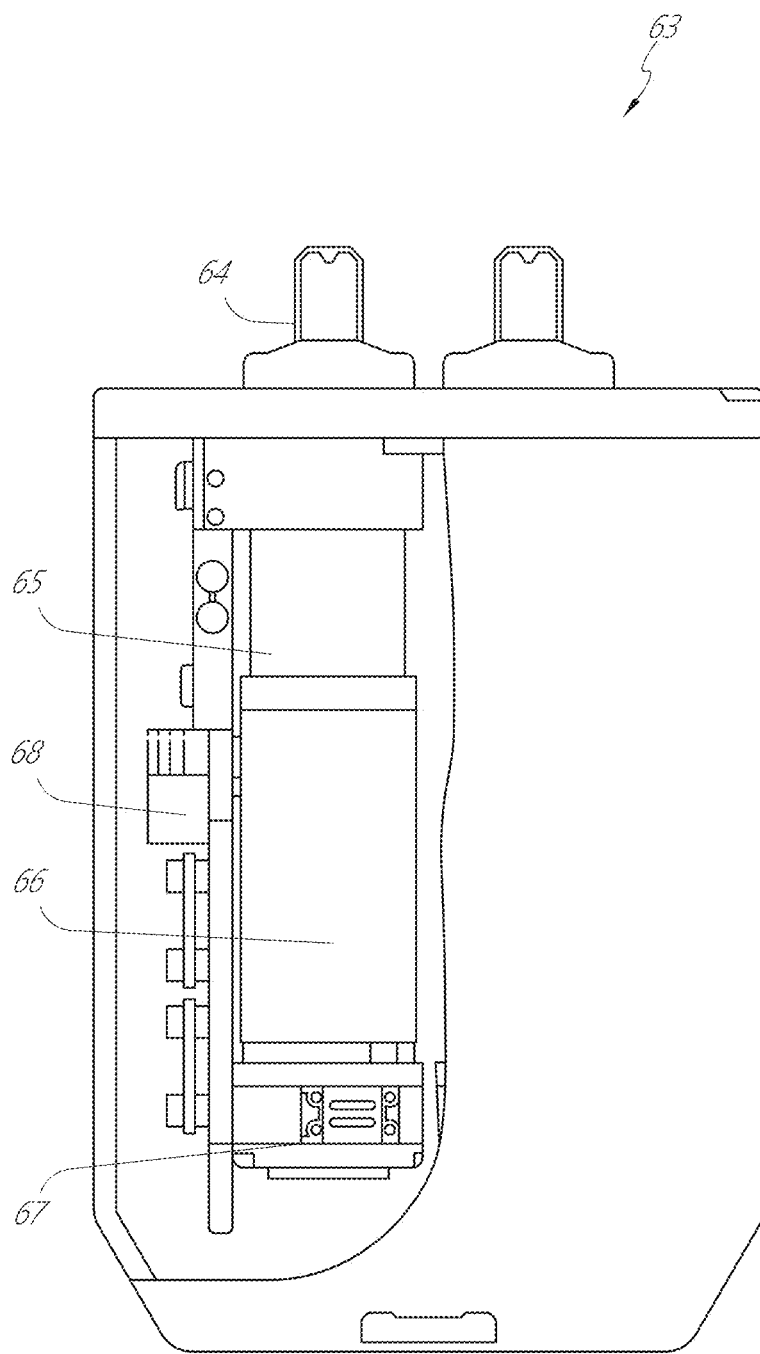
FIG. 12 illustrates an exemplary instrument driver.

FIG. 12 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 13:
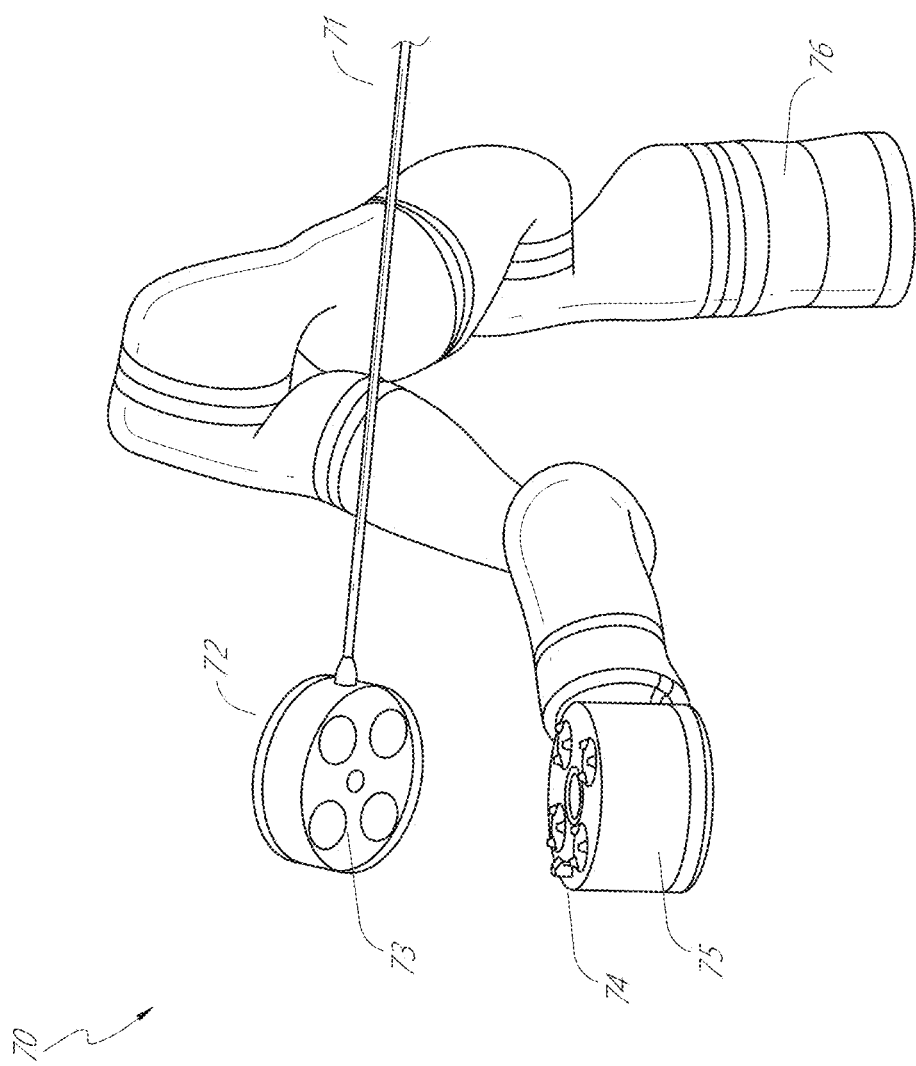
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft during an endoscopic procedure.

Figure 14:
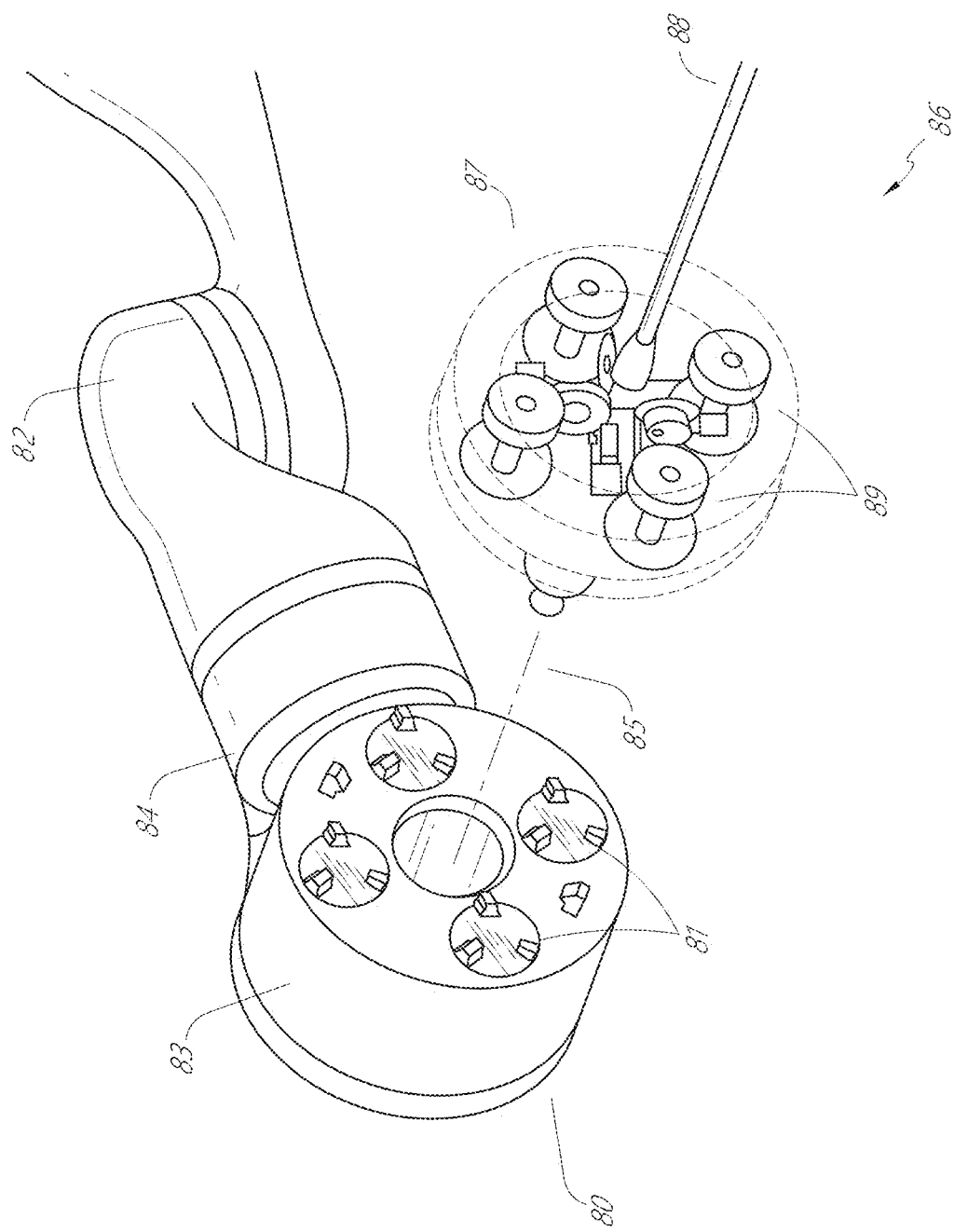
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
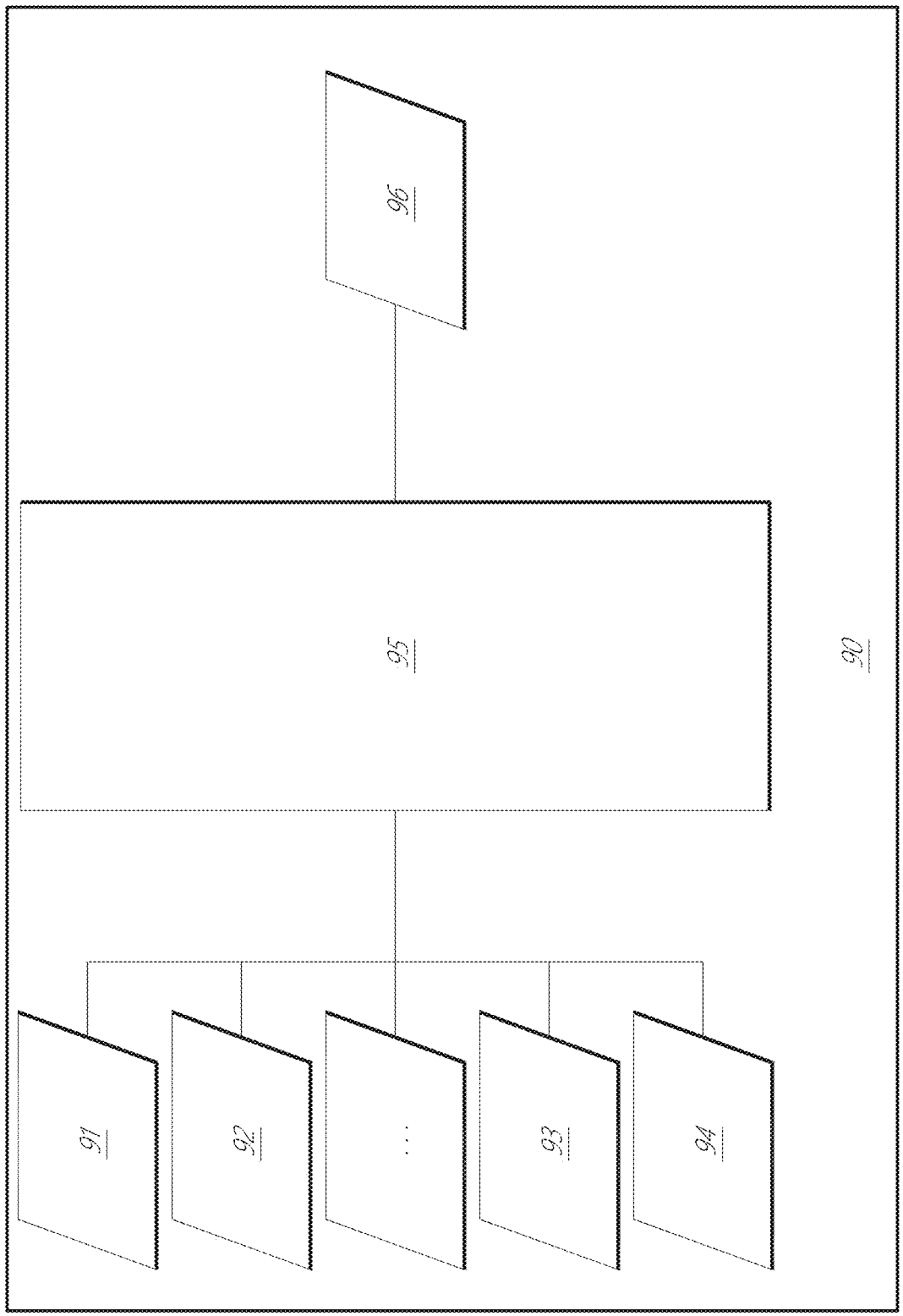
FIG. 15 depicts a block diagram illustrating a localization system that estimates a location of one or more elements of the robotic systems of FIGS. 1-10, such as the location of the instrument of FIGS. 13 and 14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator). The location data 96 may also be referred to herein as "state data" which describes a current state of the distal tip of the medical instrument with respect to a model (e.g., a skeletal model) of the anatomy of the patient. The state data may include information such as a position and orientation of the distal tip of the medical instrument for a given sample period. For example, when the patient's anatomy is modeled using a skeletal model based on a midpoint of the luminal network, the position may take the form of a segment ID and a depth along the segment.

The various input data 91-94 are now described in greater detail. Pre-operative mapping may be accomplished through the use of the collection of low dose CT scans. Pre-operative CT scans are reconstructed into three-dimensional (3D) images, which are visualized, e.g., as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a 3D volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing a shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Sensor-Based Navigation.

Embodiments of the disclosure relate systems and techniques for improving sensor-based navigation of an instrument including reducing the effects of latency introduced in displaying an indication of the location of the instrument. For example, in a surgical robotic system configured to control the position of the instrument based on received user commands, there may be a certain amount of latency between the time at which the user command(s) are received by a user input device and the display of the movement of the instrument via a display. If the latency is greater than a threshold latency value, the latency may be perceptible to the user, which can lead to a poor user experience. For example, a lower latency may be perceived as a more "responsive" system to the user than a system having a greater latency.

Since the user cannot directly observe the movement of the distal end of the instrument when the instrument is inserted into the luminal network, the user may rely on the display of the location of the instrument as an indication of the movement of the instrument. If the latency (or lag) between the user commands and the display of a corresponding change in location of the instrument is too large, the user may interpret the latency as a delay in the movement of the instrument, even when at least a portion of the delay may be attributed to the detection and processing required to determine the location of the instrument.

Accordingly, any decrease in the above-described latency may be associated with an improved user experience, by increasing the perceived responsiveness of the system to user commands. In certain implementations, it may be desirable to limit the latency to less than a threshold latency of about 300 ms.

As discussed in greater detail below, there may be a plurality of sources or causes which contribute to the overall latency. Depending on the implementation, there may be practical limits to the achievable reduction in the latency. For example, one source of latency may be the computational requirements for determining the location of the instrument based on a plurality of data sources (e.g., location sensor data, robot data, model data, etc.). Thus, aspects of this disclosure may relate to estimating a location of the instrument and displaying the estimated location prior to determining the position of the instrument based on data received from the data sources.

A. EM Navigation-Guided Bronchoscopy.

Hereinafter, an example system which may employ the techniques for estimating and displaying the location of an instrument will be described with respect to the embodiment of the estimation and display of the location of the instrument in for an EM navigation-guided bronchoscopic procedure. However, aspects of this disclosure may also apply to other location sensors which can produce location data within a corresponding location sensor coordinate system, as well as to other medical types of medical procedures.

Figure 16A:
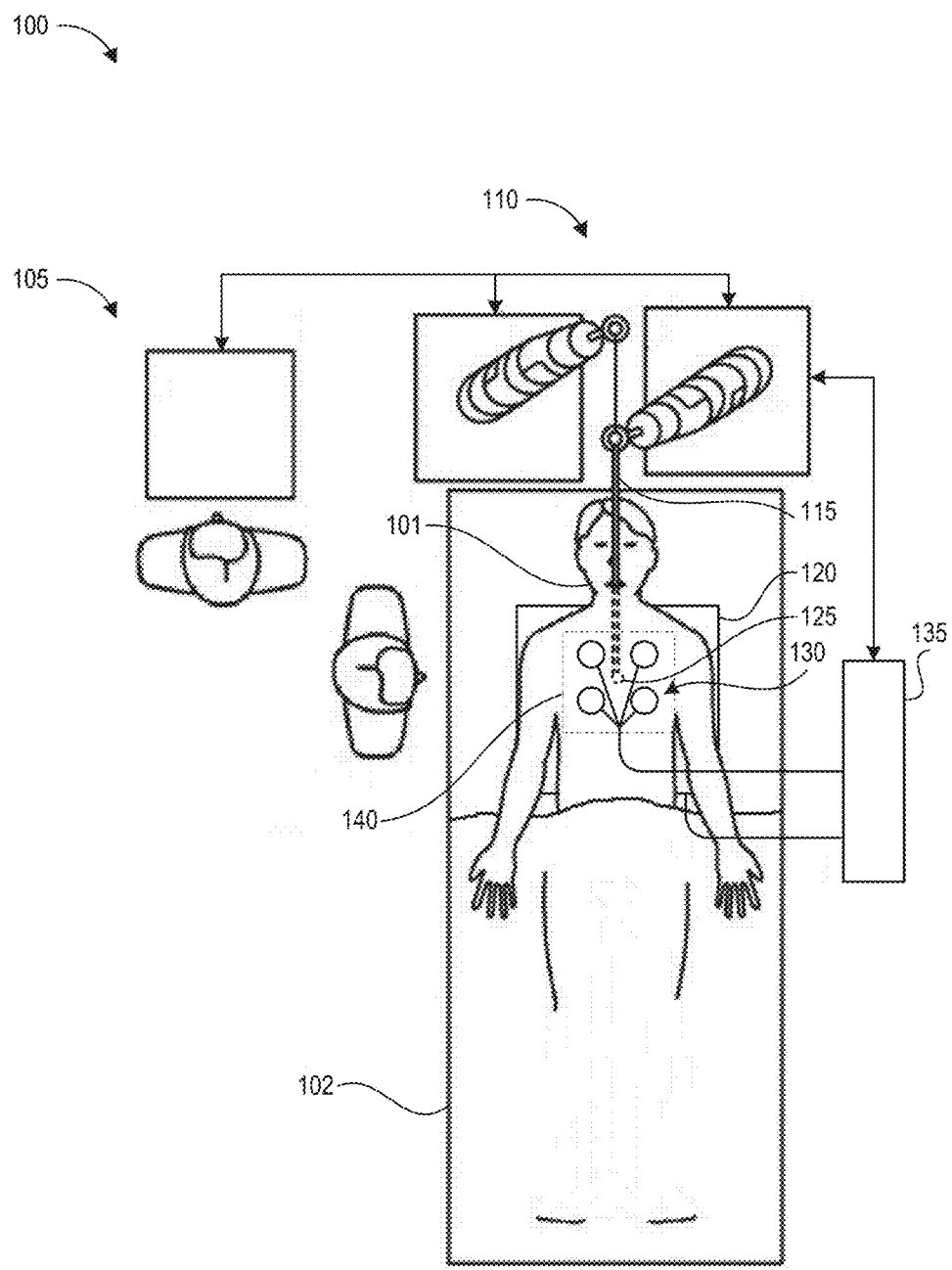
FIG. 16A illustrates an example operating environment implementing one or more aspects of the disclosed location estimation systems and techniques.

FIG. 16A illustrates an example operating environment 100 implementing one or more aspects of the disclosed location estimation systems and techniques. The operating environment 100 includes a patient 101, a platform 102 supporting the patient 101, a surgical or medical robotic system 110 guiding movement of an instrument 115, command center 105 for controlling operations of the robotic system 110, EM controller 135, EM field generator 120, and EM sensors 125, 130. FIG. 16A also illustrates an outline of a region of a luminal network 140 within the patient 101, shown in more detail in FIG. 16B.

The system 110 can include one or more robotic arms for positioning and guiding movement of instrument 115 through the luminal network 140 of the patient 101. Command center 105 can be communicatively coupled to the robotic system 110 for receiving position data and/or providing control signals from a user. As used herein, "communicatively coupled" refers to any wired and/or wireless data transfer mediums, including but not limited to a wireless wide area network (WWAN) (e.g., one or more cellular networks), a wireless local area network (WLAN) (e.g., configured for one or more standards, such as the IEEE 802.11 (Wi-Fi)), Bluetooth, data transfer cables, and/or the like. The medical robotic system 110 can be any of the systems described above with respect to FIGS. 1-15.

The instrument 115 may be a tubular and flexible surgical instrument that is inserted into the anatomy of a patient to capture images of the anatomy (e.g., body tissue) and provide a working channel for insertion of other medical instruments to a target tissue site. As described above, the instrument 115 can be a procedure-specific endoscope, for example a bronchoscope, gastroscope, or ureteroscope, or may be a laparoscope or vascular steerable catheter. The instrument 115 can include one or more imaging devices (e.g., cameras or other types of optical sensors) at its distal end. The imaging devices may include one or more optical components such as an optical fiber, fiber array, photosensitive substrate, and/or lens(es). The optical components move along with the tip of the instrument 115 such that movement of the tip of the instrument 115 results in corresponding changes to the field of view of the images captured by the imaging devices. The distal end of the instrument 115 can be provided with one or more EM sensors 125 for tracking the position of the distal end within an EM field generated around the luminal network 140.

The EM controller 135 can control EM field generator 120 to produce a varying EM field. The EM field can be time-varying and/or spatially varying, depending upon the embodiment. The EM field generator 120 can be an EM field generating board in some embodiments. Some embodiments of the disclosed systems can use an EM field generator board positioned between the patient and the platform 102 supporting the patient 101, and the EM field generator board can incorporate a thin barrier that minimizes any tracking distortions caused by conductive or magnetic materials located below it. In other embodiments, an EM field generator board can be mounted on a robotic arm, for example, similar to those shown in the robotic system 110, which can offer flexible setup options around the patient.

Figure 16B:
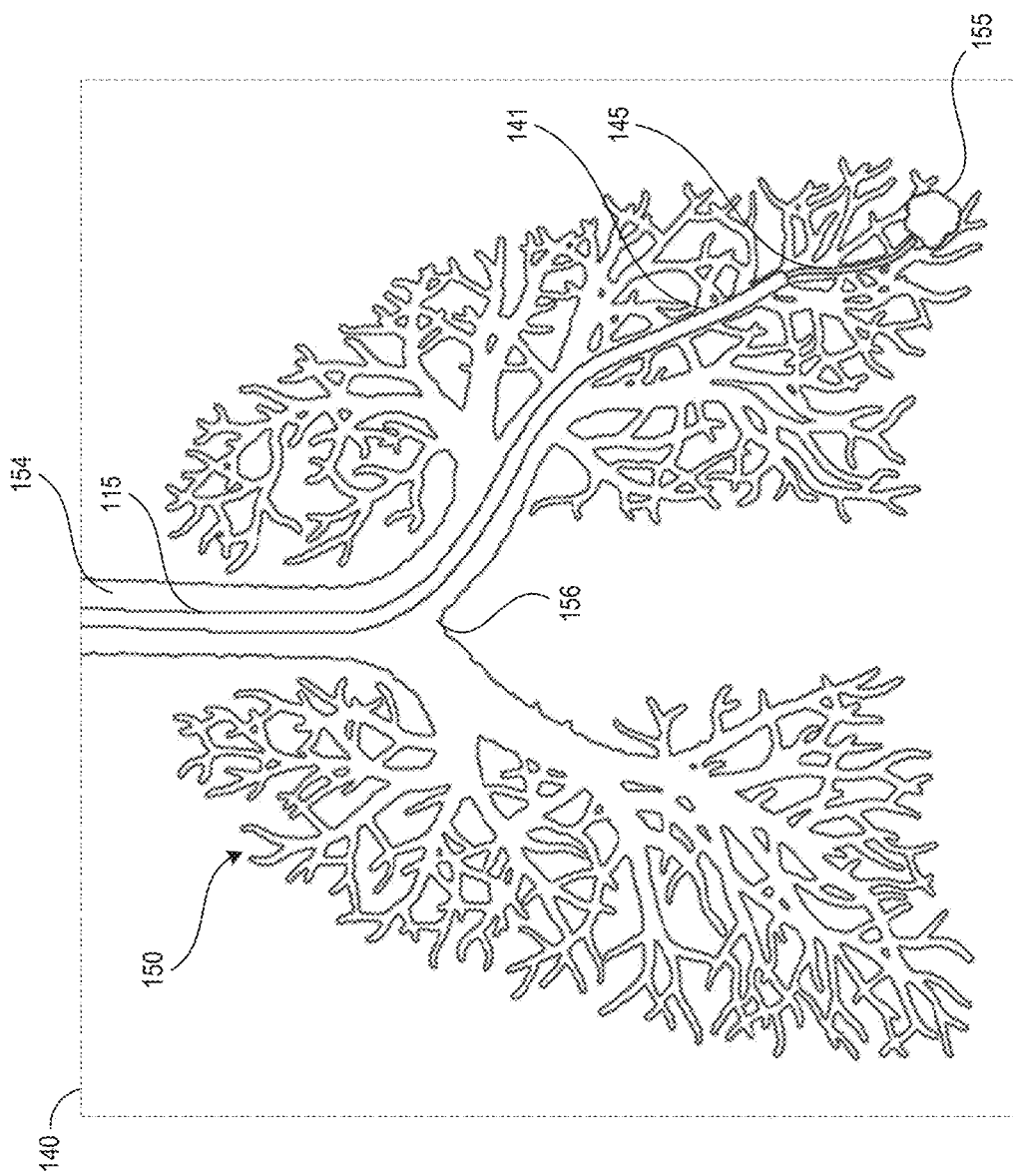
FIG. 16B illustrates an example luminal network that can be navigated in the operating environment of FIG. 16A.

FIG. 16B illustrates an example luminal network 140 that can be navigated in the operating environment 100 of FIG. 16A. The luminal network 140 includes the branched structure of the airways 150 of the patient 101, the trachea 154 leading to the main carina 156 (typically the first bifurcation encountered during bronchoscopy navigation), and a nodule (or lesion) 155 that can be accessed as described herein for diagnosis and/or treatment. As illustrated, the nodule 155 is located at the periphery of the airways 150. The instrument 115 may comprise a sheath 141 having a first diameter and thus the distal end of the sheath 141 may not able to be positioned through the smaller-diameter airways around the nodule 155. Accordingly, a scope 145 extends from the working channel of the instrument 115 and across the remaining distance to the nodule 155. The scope 145 may have a lumen through which instruments, for example, biopsy needles, cytology brushes, and/or tissue sampling forceps, can be passed to the target tissue site of nodule 155. In such implementations, both the distal end of the sheath 141 and the distal end of the scope 145 can be provided with EM sensors for tracking their respective positions within the airways 150.

In some embodiments, a 2D display of the 3D luminal network model as described herein, or a cross-section of a 3D model, can resemble FIG. 16B. Estimated position information can be overlaid onto such a representation. In certain implementations, the estimated location may be displayed on a display of a command console, such as the command console 200 illustrated in FIG. 17.

Figure 17:
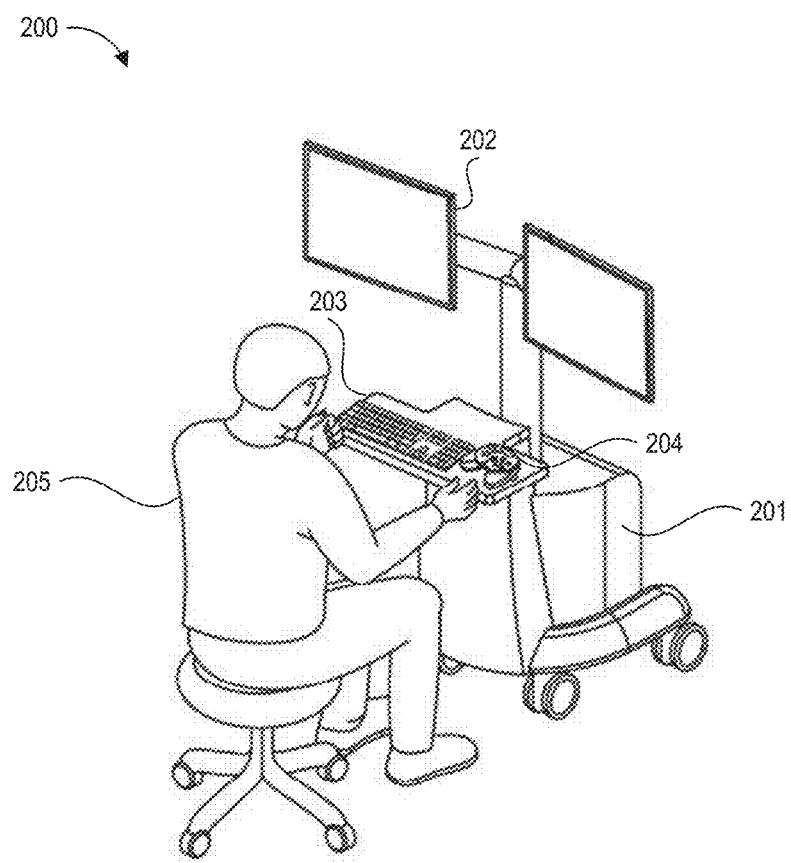
FIG. 17 illustrates an example command console that can be used, for example, as the command console in the example operating environment.

FIG. 17 illustrates an example command console 200 that can be used, for example, as the command console 105 in the example operating environment 100. The command console 200 may include a console base 201, one or more displays 202 (e.g., monitors), and one or more control modules (e.g., a keyboard 203 and joystick 204). In some embodiments, one or more of the command console 200 functionality may be integrated into a base 180 of the robotic system 110 or another system communicatively coupled to the robotic system 110. A user 205, e.g., a physician, remotely controls the robotic system 110 from an ergonomic position using the command console 200.

The console base 201 may include a central processing unit, a memory unit, a data bus, and associated data communication ports that are responsible for interpreting and processing signals such as camera imagery and tracking sensor data, e.g., from the instrument 115 shown in FIGS. 16A and 16B. In some embodiments, both the console base 201 and the base 180 perform signal processing for load-balancing. The console base 201 may also process commands and instructions provided by the user 205 through the control modules 203 and 204. In addition to the keyboard 203 and joystick 204 shown in FIG. 17, the control modules may include other devices, for example, computer mice, trackpads, trackballs, control pads, controllers such as handheld remote controllers, and sensors (e.g., motion sensors or cameras) that capture hand gestures and finger gestures. A controller can include a set of user inputs (e.g., buttons, joysticks, directional pads, etc.) mapped or linked to an operation of the instrument (e.g., articulation, driving, water irrigation, etc.).

The displays 202 may include electronic monitors (e.g., LCD displays, LED displays, touch-sensitive displays), virtual reality viewing devices, e.g., goggles or glasses, and/or other display devices. In some embodiments, the display modules 202 are integrated with the control modules, for example, as a tablet device with a touchscreen. In some embodiments, one of the displays 202 can display a 3D model of the patient's luminal network and virtual navigation information (e.g., a virtual representation of the end of the endoscope within the model based on EM sensor position) while the other of the displays 202 can display image information received from the camera or another sensing device at the end of the instrument 115. In some implementations, the user 205 can both view data and input commands to the system 110 using the integrated displays 202 and control modules. The displays 202 can display 2D renderings of 3D images and/or 3D images using a stereoscopic device, e.g., a visor or goggles. The 3D images provide an "endo view" (i.e., endoscopic view), which is a computer 3D model illustrating the anatomy of a patient. The "endo view" provides a virtual environment of the patient's interior and an expected location of an instrument 115 inside the patient. A user 205 compares the "endo view" model to actual images captured by a camera to help mentally orient and confirm that the instrument 115 is in the correct—or approximately correct—location within the patient. The "endo view" provides information about anatomical structures, e.g., the shape of airways, circulatory vessels, or an intestine or colon of the patient, around the distal end of the instrument 115. The display modules 202 can simultaneously display the 3D model and CT scans of the anatomy the around distal end of the instrument 115. Further, the display modules 202 may overlay the already determined navigation paths of the instrument 115 on the 3D model and CT scans.

In some embodiments, a model of the instrument 115 is displayed with the 3D models to help indicate a status of a surgical procedure. For example, the CT scans identify a lesion in the anatomy where a biopsy may be necessary. During operation, the display modules 202 may show a reference image captured by the instrument 115 corresponding to the current location of the instrument 115. The display modules 202 may automatically display different views of the model of the instrument 115 depending on user settings and a particular surgical procedure. For example, the display modules 202 show an overhead fluoroscopic view of the instrument 115 during a navigation step as the instrument 115 approaches an operative region of a patient.

B. Display of Estimated Instrument Location.

Figure 18:
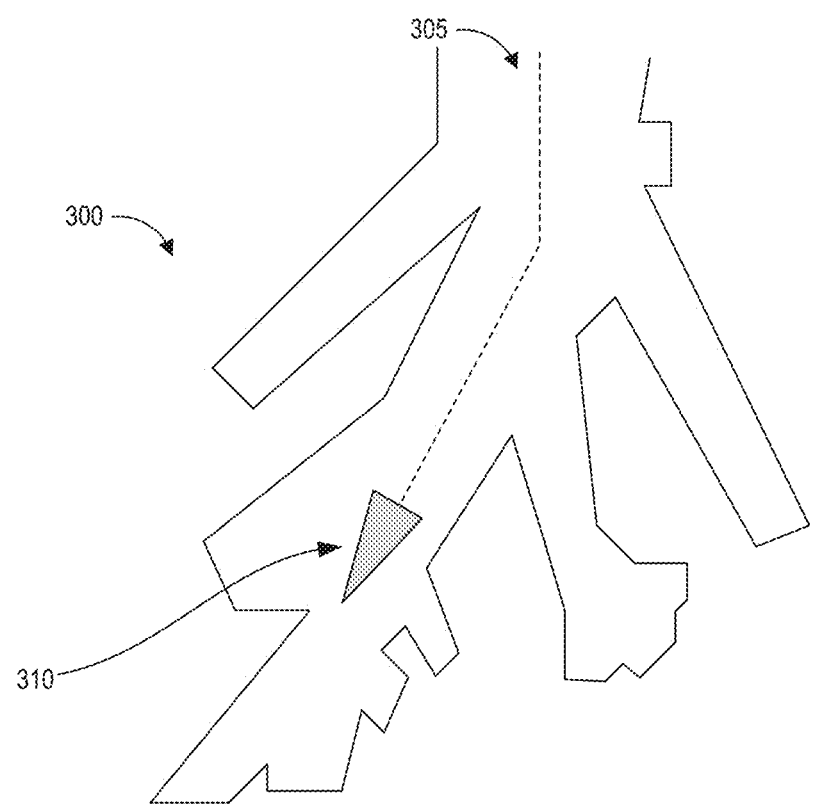
FIG. 18 illustrates a view of an example image which may be displayed during a medical procedure in accordance with aspects of this disclosure.

FIG. 18 illustrates a view of an example image which may be displayed during a medical procedure in accordance with aspects of this disclosure. In the illustrated example, a model 300 of the patient's luminal network is displayed along with a path 305 illustrating the previous positions of an instrument 310. A current location of the instrument 310 is also overlaid on the model 300 to provide feedback to a user of the system as to the current location of the instrument 310. Any suitable symbol or icon (graphical and/or textural) may be used to show one or more locations of the instrument 310. A triangle symbol is used to indicate the current location of the instrument 310 in the example of FIG. 18. The symbol may optionally be indicative of the orientation and/or direction of the instrument, depending on the shape of the symbol used to designate the location of the instrument 310.

As described above, the determination of the current location of the instrument 310 may be affected by one or more sources of latency. As used herein, the overall latency may generally refer to the period of time between the user commands received via a user input device and the state update of the location of the instrument 310, such as based on confirmation of sensor data being received from the one or more location sensors.

Figure 19:
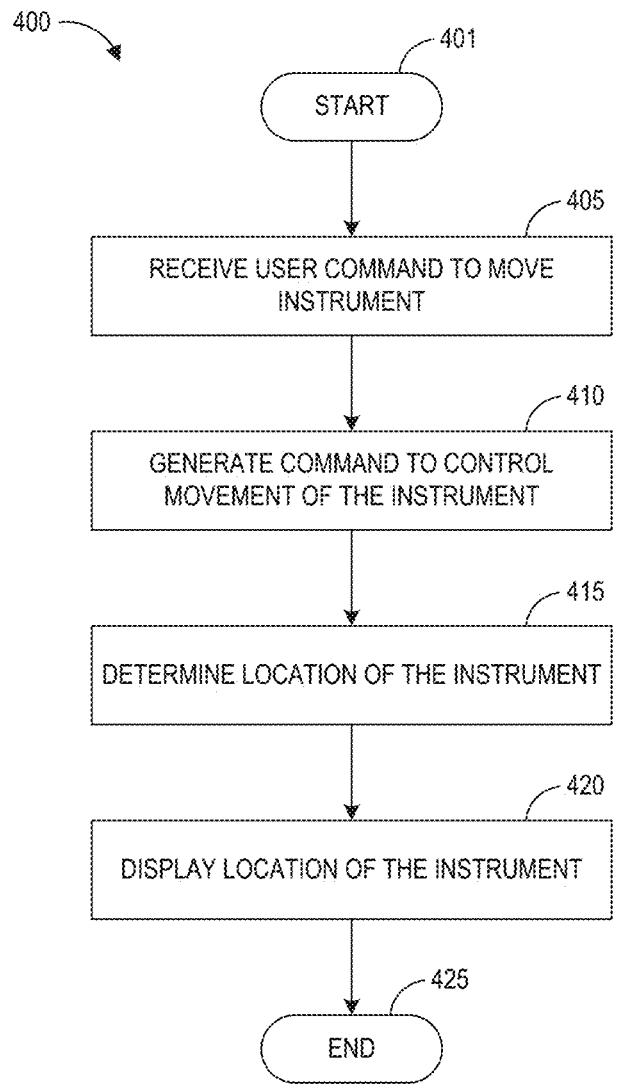
FIG. 19 is a flowchart illustrating an example method for determining a position of an instrument based on user command(s) in accordance with aspects of this disclosure.

FIG. 19 illustrates a flowchart illustrating an example technique for determining a position of an instrument based on a user command in accordance with aspects of this disclosure. The method 400 may be operable by a surgical robotic system, or component(s) thereof, for determining and displaying the location of an instrument in accordance with aspects of this disclosure. For example, the steps of method 400 illustrated in FIG. 19 may be performed by one or more processors of a surgical robotic system. For convenience, the method 400 is described as performed by a processor of the system.

The method begins at block 401. At block 405, the processor receives a user command to move the instrument. The user command may be received via a user input device which may include, for example, computer mice, trackpads, trackballs, control pads, controllers such as handheld remote controllers, and sensors (e.g., motion sensors or cameras) that capture hand gestures and finger gestures. A controller can include a set of user inputs (e.g., buttons, joysticks, directional pads, etc.) mapped to an operation of the instrument (e.g., articulation, driving, etc.). At block 410, the processor generates command(s) to control movement of the instrument based on the received user commands. The generated command(s) may include: command(s) provided to a robot controller configured to control movement of the robotic arm(s), command(s) provided to an instrument controller configured to control articulation of the instrument, etc. The robot controller and instrument articulation commands may also be provided to a navigation algorithm to be used as inputs for determining the location of the instrument and/or predicting the movement of the instrument.

At block 415, the processor determines the location of the instrument 415. In particular, the processor may use data received from a number of sources, including, e.g., the commands generated in block 410, location data received from one or more location sensors, etc., to determine the location of the distal end of the instrument. In certain implementations, the processor may employ a "fusion" algorithm which combines information indicative of the location of the distal end of the instrument received from a plurality of sources to determine the location of the instrument. One example of a fusion algorithm is the localization system 90 illustrated in FIG. 15. At block 420, the processor may display an indication of the determined location of the instrument on a display. The method ends at block 425.

Each of blocks 405-420 may involve a certain amount of delay contributing to the total latency between the time at which the user commands are received at block 405 and the time at which the location of the instrument is displayed at block 420. For example, block 405 may include or otherwise be associated with command latency (e.g., the amount of time required for movement of a joystick by a user, the amount of time required for the processor to receive and process the user command, etc.). Block 410 may have a processing delay resulting from the generating of the instrument command(s) based on the user command(s). Block 415 may include a number of sources of latency, including, for example, robot motion latency (e.g., the amount of time for actuating the commanded movements by the robotic arm (s)), flexible instrument hysteresis (e.g., physical characteristics of the instrument resulting in a certain amount of time needed to translate the forces applied to the control wires into the commanded movement at the distal end of the instrument), sensor latency, algorithm processing delay, time window filtering on sensor data, etc.

Sensor latency may depend on the specific sensors used to generate location data. For example, an EM-based location sensor may have an associated acquisition delay associated with measuring the EM field and processing the measured EM data to determine the position of the EM sensors in the EM field. Vision-based location sensors may have a delay associated with capturing images of the luminal network via one or more cameras positioned at or near the distal end of the instrument and processing the captured images to identify features that correspond to the shape of the luminal network. Certain types of location sensors may also have a time window filter applied to the data, filtering out frequencies associated with respiration, to compensate for the patient's breathing. Thus, there is a certain amount of latency required to generate data indicative of the location of the distal end of the instrument based on the type of location sensors used in the system.

Block 420 may include latency associated with transmitting images to the display and displaying the images. In some systems, the latency associated with blocks 405, 410, and 420 may be relatively low (e.g., less than 10 ms). Thus, these blocks may not introduce significant latency into the method 400. However, block 415 may introduce a relatively higher degree of latency which can affect the perceived responsiveness of the system to the user commands. In certain implementations, the location sensor latency and the instrument localization algorithm latency may have lower bounds below which it is impractical to reduce latency. For example, EM sensors may have an input latency of about 110 ms with jitter at about 25 ms. Thus, the time between a particular movement command provided to a robotic arm controller and the corresponding EM sensor event detected based on EM sensor data can be as high as 135 ms.

Moreover, the processor may apply multiple location sensor level filtering algorithms that filter the raw location sensor data and respiratory data. These filtering algorithms may add an additional latency of around 125 ms for the location sensor data filtering and more than 500 ms for the respiration filtering. There may be a lower limit to the latency introduced due to respiration filtering that is based on the frequency of respiration. That is, since the patient's respiration may be on the order of 0.2 Hz, the latency introduced due to filtering the respiration may be at least 500 ms for the filtering to sufficiently filter the respiration from the localization data. Additional processing delay(s) and jitter associated with the filtering algorithms may introduce delay on the order of about 10-20 ms.

For camera-based location sensors, the estimated latency and jitter for certain implementations may be about 150 ms, with average processing delays of about 33-50 ms. In order to use data from each of the location sensor sources, the fusion navigation algorithm may wait until the sensor data for each of the data sources is ready for processing (e.g., until the delay associated with the location sensor having the longest delay has elapsed). That is, the fusion localization algorithm may compare data received from multiple sources that corresponds to events generated at a specific time, and thus, may wait until the data for the measured time is available from each of the data sources prior to determining the location of the instrument at the specific time of the measurements. Taking into account the processing delays associated with the location sensors and the determination of the location of the instrument, the total latency between receiving the user command and displaying the location of the instrument may be greater than a threshold latency. In certain embodiments, the threshold latency may be about 300 ms, which may be based on an acceptable amount of latency for the perceived responsiveness of the system. Other values for the threshold latency may be selected in other embodiments depending on the acceptable responsiveness of the system. In certain embodiment, the threshold latency may be defined on a per-user basis, allowing the user to select a desired responsiveness of the system.

One technique for reducing the perceived latency of the display of the location of the instrument may involve estimating the location of the instrument and displaying the estimated location. When the estimation of the location of the instrument requires less processing delay than the latency of determining the location of the instrument (e.g., via block 415), then the perceived latency of the system can be reduced.

Figure 20:
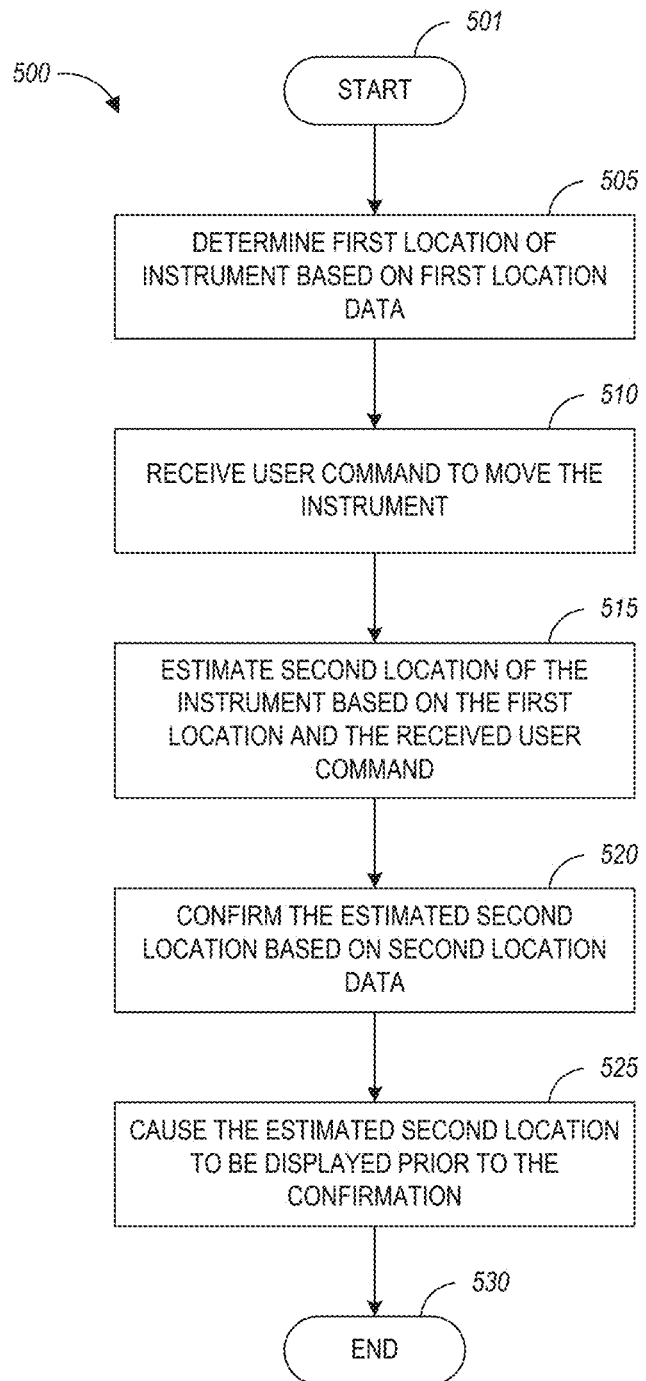
FIG. 20 is a flowchart illustrating an example method operable by a robotic system, or component(s) thereof, for estimating and displaying a location of an instrument in accordance with aspects of this disclosure.

FIG. 20 is a flowchart illustrating an example method operable by a robotic system, or component(s) thereof, for estimating and displaying a location of an instrument in accordance with aspects of this disclosure. For example, the steps of method 500 illustrated in FIG. 21 may be performed by a processor of a surgical robotic system. For convenience, the method 500 is described as performed by the processor of the system.

The method 500 begins at block 501. At block 505, the processor determines a first location of the instrument based on first location data generated by a set of one or more location sensors for the instrument. The first location data may correspond to a first time period. Thus, the processor may determine the first location of the instrument, during the first time period, based on the first location data using, for example, the localization system 90 of FIG. 15. After the first time period, at block 510, the processor receives a user command to move the instrument during a second time period. The second time period may be a time period occurring after the time period. At block 515, the processor estimates a second location of the instrument based on the first location (determined at block 505) and the received user command. The estimated second location corresponds to the second time period.

In certain implementations, the processor can estimate the location of the instrument during the second time period based on the location of the instrument at the first time period and the user command. For example, the instrument may be located within a lumen of a luminal network during the first time period and the user command may include a command to advance the instrument by a certain distance. The processor can thus estimate the location of the instrument at the second time period as being advanced along the luminal network from the first time period by the distance specified by the user command. When the luminal network branches, the processor may also estimate the location of the instrument during the second time period using additional data, such as the orientation of the instrument (e.g., the pointing direction of the instrument), the shape and orientation of the luminal network, the current articulation of the instrument, etc. The processor may be configured to predict which of the branches of the luminal network the instrument is most likely to enter and estimate the location of the instrument based on the prediction.

Accordingly, the processor may estimate the second location of the instrument based on the first location and the received user command, where the estimated second location corresponds to the second time period. At block 520, the processor confirms the estimated second location based on second location data generated by the set of location sensors. The second location data may correspond to the second time period and may be generated by the one or more location sensors during the second time period. At block 525, the processor causes the estimated second location to be displayed prior to the confirmation of the estimated second location. As used herein, confirmation occurs when the system is able to determine the location of the instrument at a given time based on the location data acquired during that time period. It is to be appreciated that, in some embodiments, when the estimated location is displayed prior to the confirmation, the total latency between receiving the user command and the display of the estimated location may be less than the amount of time between receiving the user command and confirming the estimation based on the second location data, thereby reducing the perceived responsiveness of the system. The method 500 shown in FIG. 20 ends at block 530.

Figure 21:
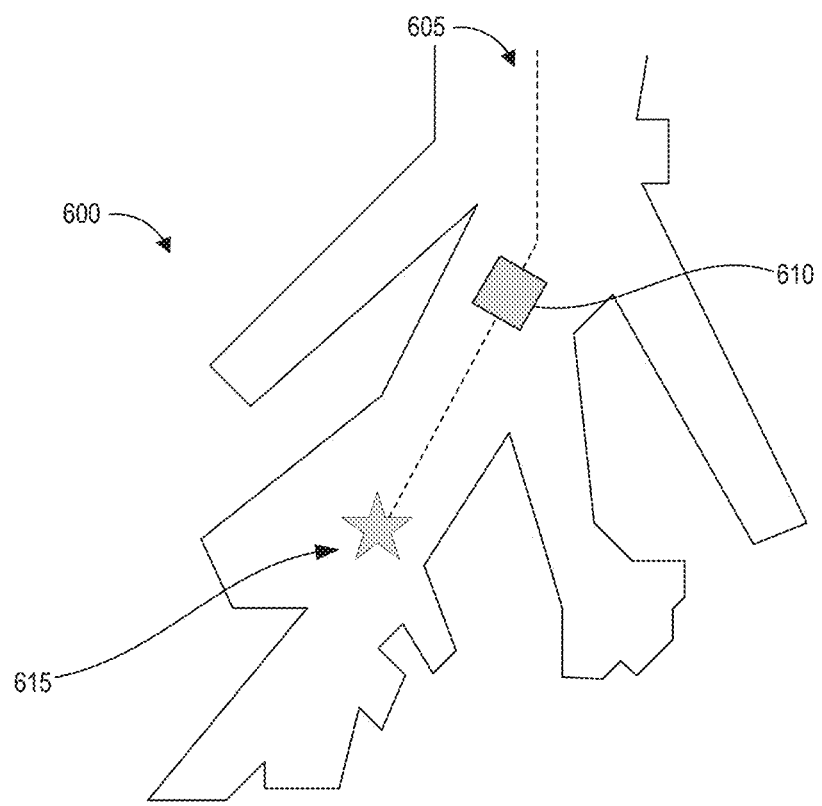
FIG. 21 illustrates another view of an example image which may be displayed during a medical procedure in accordance with aspects of this disclosure.

FIG. 21 illustrates another view of an example image which may be displayed during a medical procedure in accordance with aspects of this disclosure. In one implementation, the view illustrated in FIG. 21 may be displayed based on the processor performing the method 500 illustrated in FIG. 20. In the example illustrated in FIG. 21, a model 600 of the patient's luminal network is displayed along with a path (or trace) 605 illustrating the previous positions of the instrument. A first location 610 of the instrument may be displayed at a first time and an estimated second location 615 of the instrument may be displayed at a second time. As shown in FIG. 21, the first location 610 (shown as a square) and the estimated second location 615 (shown as a star) are positioned at different locations along the path 605. It is to be appreciated that the depictions of the first location 610 and the second location 615 are shown here are merely provided to illustrate how a location may be depicted to a user and other embodiments may use any suitable representation other than a square and a star.

In the example of FIG. 21, due to the latency of the system in determining the first location 610 using data received from the location sensors, the instrument may have advanced to the estimated second location 615 before the processor is able to confirm the location of the instrument at the first location 610 based on the data received from the location sensors during a time period corresponding to the first location 610. Accordingly, the processor may display the estimated second location 615 at the second time period based on the determined first location 610 and user command data. Here, the difference between the first time period and the second time period may be based on a processing period for the confirmation of the second location estimate. That is, in order to display the estimated second location 615 of the instrument within the threshold latency of the receipt of the user commands, the difference between the first time period associated with the first location 610 and the second time period associated with the estimated second location 615 may be commensurate with the total latency involved in determining the location of the instrument based on location sensor data.

In certain embodiments, the estimating of the second location has a first processing delay and the confirming of the estimated second location has a second processing delay. Since the techniques used to estimate the second location may be based on data that does not include large amounts of latency (e.g., does not require location sensor data), the first processing delay may be less than the second processing delay. For example, the estimation of the second location may be based on the first location data and robot insertion data, where the robot insertion data may be determined from the received user command. Since there is relatively little delay associated with generating the robot data (e.g., the latency associated with block 410 in FIG. 4), the estimation can be displayed with a latency that is less than the threshold latency associated with an acceptable amount of perceived responsiveness of the system.

Figure 22:
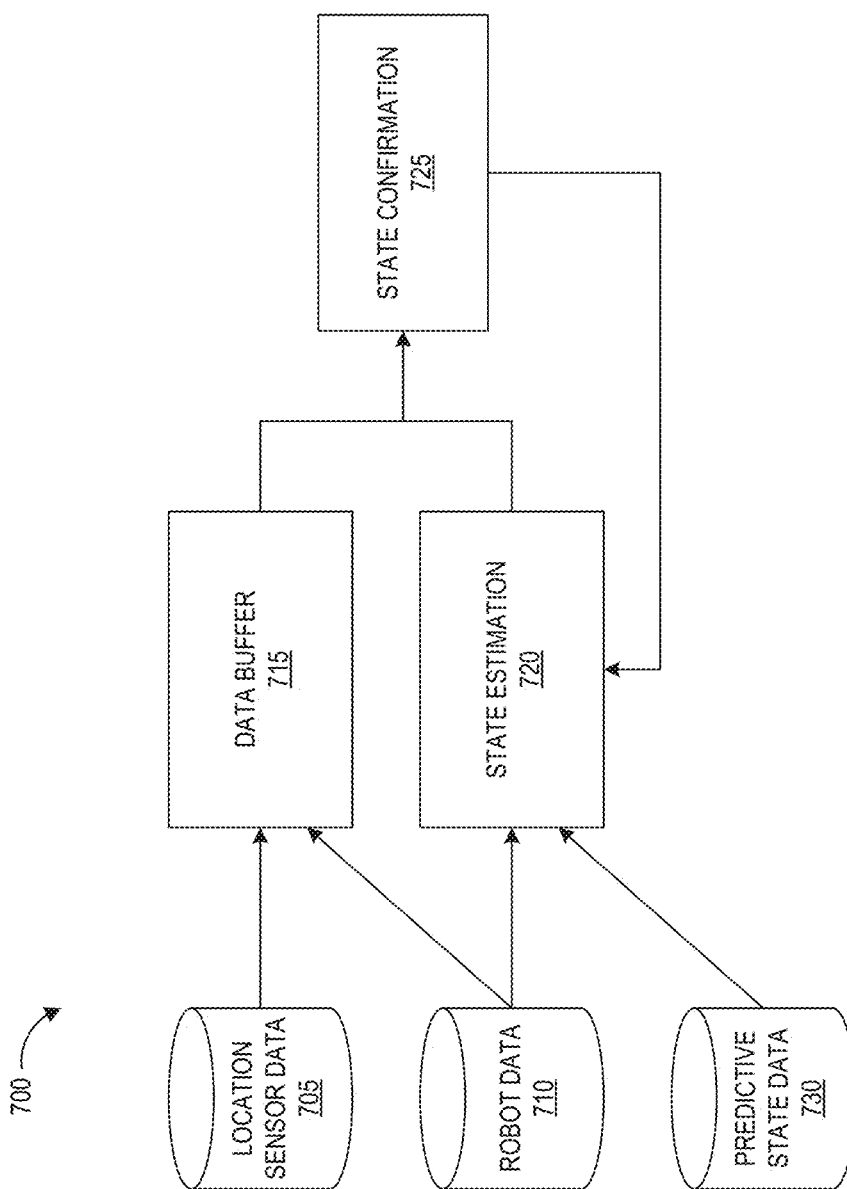
FIG. 22 depicts a block diagram illustrating one example of a system including a data buffer in accordance with aspects of this disclosure.

The system may also store a buffer of data to ensure that sufficient data is stored for both state estimation and state confirmation of the location of the instrument. FIG. 22 depicts a block diagram illustrating one example of such a system in accordance with aspects of this disclosure. Although logically separated into blocks, the functionality of the various blocks of the system 700 may be combined and/or implemented together without departing from this disclosure.

As shown in FIG. 22, location sensor data 705 and robot data 710 may be provided to a data buffer 715 and the robot data 710 may be provided to a state estimator or state estimation block 720 as the data is produced. Depending on the embodiment, the robot data 710 may include commanded data, such as an insertion amount, a roll amount, and/or an articulation amount, determined based on a user command received from a user during a corresponding time period. Although not illustrated, in embodiments where additional data other than the illustrated location sensor and robot data 705 and 710 are used by the state estimation block 720 and/or a state confirmer or state confirmation block 725, the additional data may also be supplied to the data buffer 715 and/or the state estimation block 720. The state estimation block 720 also receives confirmed state data from the state confirmation block 725. In certain embodiments, the state of the instrument as estimated by state estimation block 720 or confirmed by block 725 may include information which is indicative of the location and orientation of the instrument with respect to the model. For example, each state may include: an identification of a segment of the model of the luminal network, a insertion distance along the segment, and/or an orientation of the distal end of the instrument.

In one embodiment, each of the data buffer 715, the state estimation block 720, and the state confirmation block 725 may be implemented by a processor based on computer-executable instructions which cause the processor to perform the corresponding functionality. In another embodiment, the data buffer 715, the state estimation block 720, and the state confirmation block 725 may be executed by dedicated hardware configured to provide the corresponding functionality described herein. Alternatively, or in addition, the data buffer 715 may be implemented by a memory, register, and/or other transitory or non-transitory storage medium.

At state estimation block 720, the processor can estimate the location of the instrument based on an accurate determination of the location of the instrument at a point in the past received from state confirmation block 725. The state confirmation block 725 may involve the processor determining the state of the instrument via fusion of the buffered data (e.g., via the localization system 90 of FIG. 15) and confirming whether the determined state is consistent with a previous state estimation received from the state estimation block 720.

In certain embodiments, the system may also maintain a set of predictive states for the location of the instrument, illustrated as predictive state data 730 in FIG. 22. Each of the predictive states may be associated with a corresponding probability. Accordingly, at state estimation block 720, the processor may estimate the location of the instrument based on the predictive state received from the predictive state data 730 having the highest probability for the a corresponding time period. That is, the predictive state having the highest probability may be determined to be the most likely segment of the model of the luminal network along which the instrument was advanced during the time period. Thus, when the robot data (e.g., based on user commands) is consistent with the instrument being advanced from the current segment into a child segment, the processor may rely on the predicted state having the highest probability as the segment into which the instrument was advanced during the corresponding time period.

In some embodiments, the robot data 710 stored in the data buffer 715 may be stored as a time series with information that allows reconstruction of the estimated locations when the confirmed location for a given time differs from the estimated location. The data buffer 715 may store, for example, a time and an amount of commanded data, such as an insertion amount for a given time. When the estimated location for a time $T_n$ differs from the confirmed location for time $T_n$, the system can update the predictive states for times subsequent to time Tn (e.g., times $T_{n+1}$ through $T_c$, where time $T_c$ is the current time) based on the new confirmed location for time $T_n$ and then reconstruct the estimated locations for times subsequent to time $T_n$ using the insertion amounts in the example above and the updated predictive states.

In some implementations, the processor may be configured to adjust a speed of movement of the instrument in response to the probability of the predictive state being less than a threshold probability. For example, when the probability of the predictive state having the highest probability is less than a threshold probability, the system may not have a high confidence in the estimated location of the instrument. Accordingly, the displayed estimated location of the instrument may not be accurate, and thus, may provide misleading feedback to the user as to the location of the instrument. In this case, the processor may limit the speed of movement of the instrument so that the instrument cannot be driven too far from the current location before the location of the instrument is confirmed using location sensor data. Thus, in the case that the displayed estimate of the location is incorrect, the user will have less distance to retract the instrument to correct a potential driving of the instrument down the incorrect path.

In certain embodiments, the confirmation of the estimation of the estimated second location may include the processor comparing the second location, determined based on second location data received from the location sensors, to the estimated second location. The processor may store the second location in the memory in response to the second location being different from the estimated second location. That is, the processor may update a history indicative of the locations of the instrument during the medical procedure to reflect the location of the instrument at during the second time period as determined based on the location sensor data.

The processor may also estimate a third location of the instrument based on the estimated second location, the estimated third location corresponding to a third time period after the second time period. That is, as the system continues to move the instrument from the second location to a third location based on received user commands, the processor may update the displayed estimated location to a third location. In one example, the user command may include a command to advance the instrument, and thus, the estimated third location may correspond to the instrument being advanced down a current segment of the luminal network from the estimated second location by a distance corresponding to the user command.

However, when the second estimated location was incorrectly estimated, the estimated third location may also be incorrect. Thus, the processor may update the estimated third location based on the second location, determined based on the location data, in response to the second location being different from the estimated second location. For example, if the second location determined based on data received from location sensors is located along a different segment of the luminal network from the estimated second location, the processor may update the estimated third location using the newly determined second location and the user command.

Although the example described above in connection with the method 400 of FIG. 19 includes receiving user commands and generating commands to control the movement of the instrument via one or more robotic arms, this disclosure is not necessary limited thereto. For example, in certain implementations, the instrument may be directly controlled by the user without the use of robotic arms. In these implementations, the system may include one or more location sensors configured to generate data indicative of the location of the distal end of the instrument. The system may further include a display configured to display the location of the distal end of the instrument based on the data generated by the location sensors. As discussed above, the determination of the location of the distal end of the instrument may involve a processing delay that can contribute to latency between the movement of the instrument by the user and the display of the location of the instrument. The latency may be, in part, due to the latency of the location sensors and the processing delay required to determine the location of the instrument based on the location sensor data.

The processor may be configured to reduce the perceived latency of the display of the location of the instrument using one or more of the techniques discussed above. For example, the processor may be configured to estimate a position of the distal end of the instrument based on the most recently determined position of the instrument using the location sensor data. The processor may also be configured to incorporate one or more sources of data which may be indicative of the movement of the instrument to estimate the instrument's location. For example, the processor may be configured to determine a speed at which the instrument is being inserted, and thus, estimate the location of the instrument based on a previously determined location of the instrument and the speed of the instrument. The processor may also be configured to track the motion of the user's arm, which may be proportional to the movement of the distal end of the instrument. Thus, based on the changes in position of the user's arm, the processor may be able to estimate the change in location of the instrument from a previously determined location of the instrument. In certain embodiments, the system may include one or more additional sensors for tracking the position of the user's arms. The sensors may include, for example: a camera, gloves with embedded sensors, sensors integrated into the control mechanism of the instrument, etc.

3. Implementing Systems and Terminology.

Implementations disclosed herein provide systems, methods and apparatuses for displaying an estimated location of an instrument.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A system, comprising:
    a processor; and
    at least one computer-readable memory in communication with the processor and having stored thereon computer-executable instructions to cause the processor to:
        determine a first location of an instrument based on first location data generated by a set of one or more location sensors for the instrument, the first location data corresponding to a first time period;
        after the first time period, receive a user command to move the instrument during a second time period;
        estimate a second location of the instrument based on the first location and the received user command, the estimated second location corresponding to the second time period;
        confirm the estimated second location based on second location data generated by the set of location sensors, the second location data corresponding to the second time period; and
        cause the estimated second location to be displayed prior to the confirmation of the estimated second location.

2. The system of claim 1, wherein the difference between the first time period and the second time period is based on a processing period for the confirmation of the second location estimate.

3. The system of claim 1, wherein:
    the estimating of the second location has a first processing delay;
    the confirming of the estimated second location has a second processing delay; and
    the first processing delay is less than the second processing delay.

4. The system of claim 1, wherein the memory further has stored thereon computer-executable instructions to cause the processor to:
    estimate the first location of the instrument for the first time period; and
    confirm the estimated first location based on the first location data to determine the first location.

5. The system of claim 1, wherein the memory further has stored thereon computer-executable instructions to cause the processor to:
    maintain a set of predictive states for a predicted location of the instrument, each of the predictive states associated with a corresponding probability; and
    estimate the second location based on the predictive state having the highest probability for the second time period.

6. The system of claim 5, wherein the memory further has stored thereon computer-executable instructions to cause the processor to:
    adjust a speed of movement of the instrument in response to the probability of the predictive state being less than a threshold probability.

7. The system of claim 1, wherein the memory further has stored thereon computer-executable instructions to cause the processor to:
    receive second location data from set of the location sensors during the second time period, wherein the confirming of the estimated second location comprises determining the second location of the instrument based on the second location data; and cause the estimated second location to be displayed prior to determining the second location based on the second location data.

8. The system of claim 7, wherein the memory further has stored thereon computer-executable instructions to cause the processor to:
compare the second location to the estimated second location; and
store the second location in the memory in response to the second location being different from the estimated second location.

9. The system of claim 8, wherein the memory further has stored thereon computer-executable instructions to cause the processor to:
estimate a third location of the instrument based on the estimated second location, the estimated third location corresponding to a third time period after the second time period; and
update the estimated third location based on the second location in response to the second location being different from the estimated second location.

10. The system of claim 1, wherein the set of location sensors comprises at least one of an electromagnetic (EM) sensor, a shape-sensing fiber, and a camera.

11. A non-transitory computer readable storage medium having stored thereon instructions that, when executed, cause at least one computing device to:
determine a first location of an instrument based on first location data generated by a set of one or more location sensors for the instrument, the first location data corresponding to a first time period;
after the first time period, receive a user command to move the instrument during a second time period;
estimate a second location of the instrument based on the first location and the received user command, the estimated second location corresponding to the second time period;
confirm the estimated second location based on second location data generated by the set of location sensors, the second location data corresponding to the second time period; and
cause the estimated second location to be displayed prior to the confirmation of the estimated second location.

12. The non-transitory computer readable storage medium of claim 11, wherein the difference between the first time period and the second time period is based on a processing period for the confirmation of the second location estimate.

13. The non-transitory computer readable storage medium of claim 11, wherein:
the estimating of the second location has a first processing delay;
the confirming of the estimated second location has a second processing delay; and
the first processing delay is less than the second processing delay.

14. The non-transitory computer readable storage medium of claim 11, further having stored thereon instructions that, when executed, cause at least one computing device to:
estimate the first location of the instrument for the first time period; and
confirm the estimated first location based on the first location data to determine the first location.

15. The non-transitory computer readable storage medium of claim 11, further having stored thereon instructions that, when executed, cause at least one computing device to:
maintain a set of predictive states for a predicted location of the instrument, each of the predictive states associated with a corresponding probability; and
estimate the second location based on the predictive state having the highest probability for the second time period.

16. The non-transitory computer readable storage medium of claim 15, further having stored thereon instructions that, when executed, cause at least one computing device to:
adjust a speed of movement of the instrument in response to the probability of the predictive state being less than a threshold probability.

17. The non-transitory computer readable storage medium of claim 11, further having stored thereon instructions that, when executed, cause at least one computing device to:
receive second location data from set of the location sensors during the second time period, wherein the confirming of the estimated second location comprises determining the second location of the instrument based on the second location data; and
cause the estimated second location to be displayed prior to determining the second location based on the second location data.

18. The non-transitory computer readable storage medium of claim 17, further having stored thereon instructions that, when executed, cause at least one computing device to:
compare the second location to the estimated second location; and
store the second location in the memory in response to the second location being different from the estimated second location.

19. The non-transitory computer readable storage medium of claim 18, further having stored thereon instructions that, when executed, cause at least one computing device to:
estimate a third location of the instrument based on the estimated second location, the estimated third location corresponding to a third time period after the second time period; and
update the estimated third location based on the second location in response to the second location being different from the estimated second location.

20. The non-transitory computer readable storage medium of claim 11, wherein the set of location sensors comprises at least one of an electromagnetic (EM) sensor, a shape-sensing fiber, and a camera.

21. A method of displaying an estimated location of an instrument, comprising:
determining a first location of the instrument based on first location data generated by a set of one or more location sensors for the instrument, the first location data corresponding to a first time period;
after the first time period, receiving a user command to move the instrument during a second time period;
estimating a second location of the instrument based on the first location and the received user command, the estimated second location corresponding to the second time period;
confirming the estimated second location based on second location data generated by the set of location sensors, the second location data corresponding to the second time period; and
causing the estimated second location to be displayed prior to the confirmation of the estimated second location.

22. The method of claim 21, wherein the difference between the first time period and the second time period is based on a processing period for the confirmation of the second location estimate.

23. The method of claim 21, wherein:
the estimating of the second location has a first processing delay;
the confirming of the estimated second location has a second processing delay; and
the first processing delay is less than the second processing delay.

24. The method of claim 21, further comprising:
estimating the first location of the instrument for the first time period; and
confirming the estimated first location based on the first location data to determine the first location.

25. The method of claim 21, further comprising:
maintaining a set of predictive states for a predicted location of the instrument, each of the predictive states associated with a corresponding probability; and
estimating the second location based on the predictive state having the highest probability for the second time period.

26. The method of claim 25, further comprising:
adjusting a speed of movement of the instrument in response to the probability of the predictive state being less than a threshold probability.

27. The method of claim 21, further comprising:
receiving second location data from set of the location sensors during the second time period, wherein the confirming of the estimated second location comprises determining the second location of the instrument based on the second location data; and
causing the estimated second location to be displayed prior to determining the second location based on the second location data.

28. The method of claim 27, further comprising:
comparing the second location to the estimated second location; and
storing the second location in the memory in response to the second location being different from the estimated second location.

29. The method of claim 28, further comprising:
estimating a third location of the instrument based on the estimated second location, the estimated third location corresponding to a third time period after the second time period; and
updating the estimated third location based on the second location in response to the second location being different from the estimated second location.

30. The method of claim 21, wherein the set of location sensors comprises at least one of an electromagnetic (EM) sensor, a shape-sensing fiber, and a camera.

* * * * *